US009889115B2

(12) United States Patent
Erickson et al.

(10) Patent No.: US 9,889,115 B2
(45) **Date of Patent: *Feb. 13, 2018**

(54) FITNESS ASSAY AND ASSOCIATED METHODS

(71) Applicants: The United States of America, as represented by the Secretary, Department of Health and Human Services, Washington, DC (US); Board of Trustees of the University of Illinois, Urbana, IL (US)

(72) Inventors: John W. Erickson, Potomac, MD (US); Sergei V. Gulnik, Frederick, MD (US); Hiroaki Mitsuya, Chevy Chase, MD (US); Arun E. Ghosh, West Lafayette, IN (US)

(73) Assignees: Board of Trustees of the University of Illinois, Urbana, IL (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 347 days.

This patent is subject to a terminal disclaimer.

(21) Appl. No.: 13/933,319

(22) Filed: Jul. 2, 2013

(65) Prior Publication Data

US 2014/0011815 A1 Jan. 9, 2014

Related U.S. Application Data

(63) Continuation of application No. 11/870,931, filed on Oct. 11, 2077, now Pat. No. 8,597,876, which is a (Continued)

(51) Int. Cl.
*A61K 31/341* (2006.01)
*A61K 31/34* (2006.01)
(Continued)

(52) U.S. Cl.
CPC ............ *A61K 31/341* (2013.01); *A61K 31/34* (2013.01); *A61K 31/343* (2013.01); *A61K 31/35* (2013.01);
(Continued)

(58) Field of Classification Search
None
See application file for complete search history.

(56) References Cited

U.S. PATENT DOCUMENTS 5,475,027 A 12/1995 Talley et al.
5,502,060 A 3/1996 Thompson
(Continued)

FOREIGN PATENT DOCUMENTS

EP 0 337 714 A2 10/1989
EP 0 434 365 A2 6/1991
(Continued)

OTHER PUBLICATIONS

U.S. Appl. No. 11/870,931, filed Oct. 11, 2007.
(Continued)

*Primary Examiner* — Jeffrey S Lundgren
*Assistant Examiner* — Stephanie Springer
(74) *Attorney, Agent, or Firm* — Leydig, Voit & Mayer, Ltd.

(57) ABSTRACT

The present invention provides an assay for determining the biochemical fitness of a biochemical species in a mutant replicating biological entity relative to its predecessor. The present invention further provides a continuous fluorogenic assay for measuring the anti-HIV protease activity of protease inhibitor. The present invention also provides a method of administering a therapeutic compound that reduces the chances of the emergence of drug resistance in therapy. The present invention also provides a compound of formula (I) or a pharmaceutically acceptable salt, a prodrug, a composition, or an ester thereof, wherein A is a group of formulas (A), (B), (C) or (D); $R^1$, $R^2$, $R^3$, $R^5$ or $R^6$ is H, or an optionally substituted and/or heteroatom-bearing alkyl, alkenyl, alkynyl, or cyclic group; Y and/or Z are $CH_2$, O, S, SO, $SO_2$, amino, amides, carbamates, ureas, or thiocarbonyl derivatives thereof, optionally substituted with an alkyl, alkenyl, or alkynyl group; n is from 1 to 5; X is a bond, an optionally substituted methylene or ethylene, an amino, O or S; Q is C(O), C(S), or $SO_2$; m is from 0 to 6; $R^4$ is OH, =O (keto), $NH_2$, or alkylamino, including esters, amides, and salts thereof; and W is C(O), C(S), S(O), or $SO_2$. Optionally, $R^5$ and $R^6$, together with the N—W bond of formula (I), comprise a macrocyclic ring.

(I)

(A)

(Continued)

-continued

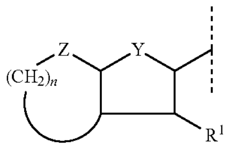

(B)

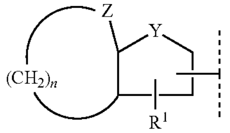

(C)

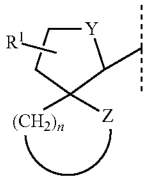

(D)

6 Claims, 5 Drawing Sheets

Related U.S. Application Data continuation of application No. 09/720,276, filed as application No. PCT/US99/14119 on Jun. 23, 1999, now Pat. No. 7,470,506.

(60) Provisional application No. 60/090,393, filed on Jun. 23, 1998.

(51) Int. Cl.

| | |
|---|---|
| ***A61K 31/35*** | (2006.01) |
| ***A61K 31/426*** | (2006.01) |
| ***A61K 31/4523*** | (2006.01) |
| ***A61K 31/4525*** | (2006.01) |
| ***A61K 31/47*** | (2006.01) |
| ***C12Q 1/02*** | (2006.01) |
| ***C12Q 1/37*** | (2006.01) |
| ***A61K 31/343*** | (2006.01) |
| ***A61K 31/427*** | (2006.01) |
| ***A61K 31/4725*** | (2006.01) |
| ***A61K 31/496*** | (2006.01) |

(52) U.S. Cl.

CPC .......... *A61K 31/426* (2013.01); *A61K 31/427* (2013.01); *A61K 31/4523* (2013.01); *A61K 31/4525* (2013.01); *A61K 31/47* (2013.01); *A61K 31/4725* (2013.01); *A61K 31/496* (2013.01); *C12Q 1/025* (2013.01); *C12Q 1/37* (2013.01); *G01N 2333/16* (2013.01); *G01N 2333/8142* (2013.01)

(56) References Cited

U.S. PATENT DOCUMENTS

| | | | |
|---|---|---|---|
| 5,585,397 | A | 12/1996 | Tong et al. |
| 5,691,372 | A | 11/1997 | Tung et al. |
| 5,703,076 | A | 12/1997 | Talley et al. |
| 5,705,500 | A | 1/1998 | Getman et al. |
| 5,723,490 | A | 3/1998 | Tung |
| 5,728,718 | A | 3/1998 | Randad et al. |
| 5,744,481 | A | 4/1998 | Vazquez et al. |
| 5,753,660 | A | 5/1998 | Sikorski et al. |
| 5,766,842 | A | 6/1998 | Heefner et al. |
| 5,843,946 | A | 12/1998 | Vazquez et al. |
| 6,060,476 | A | 5/2000 | Vazquez et al. |
| 6,251,874 | B1 | 6/2001 | Lisziewicz et al. |
| 7,470,506 | B1 | 12/2008 | Erickson et al. |
| 7,700,645 | B2 | 4/2010 | Vermeersch et al. |
| 8,518,987 | B2 | 8/2013 | Vermeersch |
| 8,597,876 | B2 | 12/2013 | Erickson et al. |
| 2005/0158713 | A1 | 7/2005 | Erickson et al. |

FOREIGN PATENT DOCUMENTS

| | | | |
|---|---|---|---|
| EP | 0 528 661 | A2 | 2/1993 |
| EP | 0 534 511 | A1 | 3/1993 |
| EP | 0 539 192 | B1 | 4/1993 |
| EP | 0 550 924 | A1 | 7/1993 |
| GB | 2276621 | A | 10/1994 |
| JP | A-H10-505324 | | 5/1998 |
| WO | WO 90/09191 | A1 | 8/1990 |
| WO | WO 94/04492 | A1 | 3/1994 |
| WO | WO 94/05639 | A1 | 3/1994 |
| WO | WO 94/14793 | A1 | 7/1994 |
| WO | WO 95/06030 | A1 | 3/1995 |
| WO | WO 95/33464 | | 12/1995 |
| WO | WO 96/28463 | A1 | 9/1996 |
| WO | WO 97/01349 | A1 | 1/1997 |
| WO | WO 97/19055 | A1 | 5/1997 |
| WO | WO 98/20888 | | 5/1998 |
| WO | WO 99/65870 | A2 | 12/1999 |
| WO | WO 99/67254 | A2 | 12/1999 |
| WO | WO 99/67417 | A2 | 12/1999 |
| WO | WO 00/48466 | A2 | 8/2000 |

OTHER PUBLICATIONS

U.S. Appl. No. 09/720,276, filed Mar. 7, 2001.

Bone et al., "X-ray Crystal Structure of the HIV Protease Compara. With L700,417, an Inhibitor with Pseudo $C_2$ Symmetry," *J. Am. Chem. Soc.*, 113: 9382 (1991).

Borman et al., "Resistance of human immunodeficiency virus type 1 to protease inhibitors: selection of resistance mutations in the presence and absence of the drug." *J. Gen. Virology*, 77(3): 419-426 (Mar. 1996).

Chakraborty et al., "2,5-Anhydro sugar diacid and 2,5-anhydro sugar diamine based $C_2$ cymmetric peptidomimetics, as potential HIV-1 protease inhibitors," *Tetrahedron Letters*, 41: 10121-10125 (2000).

Civil Docket for Case 2:10-cv-01461-WHW-CCC, 1-3, Downloaded Jun. 6, 2011.

Civil Docket for Case 2:10-cv-05956-WHW-MAS, 1-8, Downloaded Jun. 3, 2011.

Civil Docket for Case 2:11-cv-01750-WHW-CCC, 1-4, Downloaded Jun. 3, 2011.

Complaint for Patent Infringement, Case 2:10-cv-01461-WHW-CCC, Document 1, Filed Mar. 15, 2011.

Complaint for Patent Infringement, Case 2:10-cv-05956-WHW-CCC, Document 1, 1-11, Filed Nov. 15, 2010.

Complaint for Patent Infringement, Case 2:11-cv-01750-WHW-CCC, Document 1, 1-41, Filed Mar. 28, 2011.

Defendant Mylan Pharmaceuticals Inc.'s Answers, Defenses, and Counterclaims, Case 2:10-cv-05956-WHW-MAS, Document 15, 1-17, Filed Mar. 21, 2011.

Defendants Lupin Limited's and Lupin Pharmaceuticals Inc.'s Answers, Defenses, and Counterclaims, Case 2:10-cv-05956-WHW-MAS, Document 17, 1-17, Filed Mar. 21, 2011.

Defendants' Reply in Support of Their Motion to Stay, Case 2:10-cv-05956-WHW-MAS, Document 33, 1-15, Filed May 2, 2011.

Erickson et al., "Design, Activity, and 2.8 A Crystal Structure of a $C_2$ Symmetric Inhibitor Complexed to HIV-1 Protease," *Science*, 249: 527-533 (1990).

European Patent Office: Communication of a Notice of Opposition in European Patent Application No. 99931861.1 (Dec. 14, 2011).

(56) References Cited

OTHER PUBLICATIONS

European Patent Office: Communication of Notices of Opposition (R. 79(1) EPC) dated Jan. 13, 2012.
European Search Report, Application No. 10179052.5, dated Apr. 5, 2011.
Fahey et al., "Status of Immune-based therapies in HIV infection and ADIS," *Clinical and Experimental Immunology*, 88, 1-5 (1992).
Fox, "No Winner against AIDS," *Bio/Technology*, 12, 138 (Feb. 1994).
Ghosh et al, "Rational Design of Potent Nonpeptidal HIV Protease Inhibitors," *210th American Chem. Soc. Nat'l Meeting*, Medi 27 (Aug. 20-24, 1995).
Ghosh et al. "Structure Based Design: Novel Spirocyclic Ethers as Nonpeptidal, $P_2$ -Ligands for HIV protease Inhibitors," *Bioorganic & Med. Chem. Lett.*, 8: 979-982 (1998).
Ghosh et al., "Design and Synthesis of High Affinity Ligands for HIV Protease Inhibitors," *207th American Chem. Soc. Nat'l Meeting*, Medi 37 (Mar. 13-17, 1994).
Ghosh et al., "A Stereoselective Synthesis of the Hydroxyethylene Dipeptide Isostere," *216th American Chem. Soc. Nat'l Meeting*, Medi 229 (1998).
Ghosh et al., "Antiviral Activity of UIC-94-003, a Novel Inhibitor of the Human Immuno deficiency Virus type 1 Protease," *39th Interscience Conference on Antimicrobial Agents and Chemotherapy*, San Francisco, Calif., Session 89F, paper 928 (Sep. 26-29, 1999).
Ghosh et al., "Design of Anti-resistance HIV-1 Protease inhibitors," *Antiviral Research*, 51: 26, Abstract 035 (2001).
Ghosh et al., "Cyclic Sulfone-3-Carboxamides as Novel $P_{2-}$ Ligands for Ro 31-8959 Based HIV-1 Protease Inhibitors," *Bioorganic & Med. Chem. Lett.*, 5(1): 83-88 (1995).
Ghosh et al., "Potent HIV Protease Inhibitors Incorporating High-Affinity $P_2$ -Ligands and (R)-(Hydroxyethyllamino)Sulfonamide Isostere," *Bioorganic & Medicinal Chemistry Letters*, 8: 687-690 (Mar. 1998).
Ghosh et al., "HIV-1 Protease Inhibitors: Synthesis and Biological Evaluation of Glycopeptidemimetics," *Drug Design and Discovery*, 10: 77-88 (1993).
Ghosh et al., "Structure-based design of non-peptide HIV protease inhibitors," *II Farmaco*, 56: 29-32 (2001).
Ghosh et al., "Cyclic Sulfolan. as Novel and High Affinity $P_2$ Ligands for HIV-1 Protease Inhibitors," *J. Med. Chem.*, 36: 924-927 (1993).
Ghosh et al., "Nonpeptidal $P_2$ Ligands for HIV Protease Inhibitors: Structure-Based Design, Synthesis, and Biological Evaluation," *J. Med. Chem.*, 39: 3278-3290 (1996).
Ghosh et al., "Structure-Based Design: Potent inhibitors of Human Brain Memapsin2 (β Secretase)," *J. Med. Chem.*, 44: 2865-2868 (2001).
Ghosh et al., "Potent HIV protease inhibitors: the development of tetrahydrofuranylglycines as novel P2-ligands and pyrazine amides as P3-ligands," *J. Medicinal Chemistry*, 36(16): 2300-2310 (Aug. 1993).
Ghosh et al., "3-Tetrahydrofuras and Pyran Urethanes as High-Affinity $P_2$ -Ligands for HIV-1 Protease Inhibitors," *J. Medicinal Chemistry*, 36(2): 292-294 (Jan. 1993).
Ghosh et al., "Structure-based design of HIV-1 protease inhibitors: replacement of two amides and a 10 piaromatic system by a fused bis-tetrahydrofuran," *J. Medicinal Chemistry*, 37(16): 2506-2508 (Aug. 1994).
Ghosh et al., "The Development of Cyclic Sulf lanes as Novel and High-Affinity $P_2$ Ligands for HIV-1 Protease Inhibitors," *J. Medicinal Chemistry*, 37: 1177-1188 (Apr. 1994).
Ghosh et al., "Synthesis and Optical Resolution of High Affinity $P_2$ -Ligands for HIV-1 Protease Inhibitors," *Tetrahedron Letters*, 36(4): 505-508 (1995).
Ghosh et al., "Ring-Closing Metathesis Strategy to Unsaturated γ and δ -Lactones: Synthesis of Hydroxyethylene Isostere for Protease Inhibitors," *Tetrahedron Letters*, 39: 4651-4654 (1998).
Gulnik et al. "Kinetic characterization and Cross-Resistance Patterns of HIV-1 Protease Mutants Selected under Drug Pressure," *Biochemistry*, 34(29): 9282-9287 (Jul. 1995).
Ho et al., "Characterization of Human Immunodeficiency Virus Type 1 Variants with Increased Resistance to a $C_2$ -Symmetric Protease Inhibitor," *J. Virology*, 68(3): 2016-2020 (Mar. 1994).
Holloway et al., "A Priori Prediction of Activity for HIV-1 Protease Inhibitors Employing Energy Minimization in the Active Site,", *J. Med. Chem.*, 38, 305-317 (1995).
Hong et al., "Cellular Immunology," *Science*, 290(5489): 150-153 (Oct. 6, 2000).
Huff et al., "The Design and Synthesis of Orally Bioavailable HIV-1 Protease Inhibitors," *Journal of Cellular Biochemistry*, 130, S 037 (Feb. 26-Apr. 17, 1994).
Huff, "HIV Protease: A Novel Chemotherapeutic target for AIDS," *J. Med. Chem.*, 34(8): 2305-2314 (Aug. 1991).
Jadav et al., "Cyclic Urea Amides: HIV-1 Protease Inhibitors with Low Nanomolar Potency against both Wild Type and Protease Inhibitor Resistance Mutants of HIV," *J. Med. Chem*, 40, 181-191 (1997).
Japanese Patent Office: Office Action in Japanese Patent Application No. 266865/2009 (Dec. 20, 2011).
Kageyama et al., "In Vitro Inhibition of Human Immunodeficiency Virus (HIV) Type 1 Replication by $C_2$ Symmetry-Based HIV Protease Inhibitors as Single Agents or in Combinations," *Antimicrob Agents Chemother.*, 36: 926-933 (May 1992).
Kaplan et al., "Selection of multiple human immunodeficiency virus type 1 variants that encode viral proteases with decreased sensitivity to an inhibitor of the viral protease," *PNAS USA*, 91: 5597-5601 (1994).
Kim et al., "Crystal Structure of HIV-1 Protease in Complex with VX-478, a Potent and Orally Bioavailable Inhibitor of the Enzyme," *J. Medicinal Chemistry*, 38(17): 1181-1182 (1995).
Klabe et al., "Resistance to HIV Protease Inhibitors: A Comparison of Enzyme Inhibition and Antiviral Potency," *Biochemistry*, 37(24): 8735-8742 (May 1998).
Koh et al., "Structures of HIC-94017 and amprenavir," *Antimicrob. Agents Chemother.*, 47: 3123-3129 (2003).
Kramer et al., "HTLV-III gag Protein Is Processed in Yeast Cells by the Virus pol-Protease," *Science*, 231: 1580-1584 (1996).
Lascar et al., "Role of darunavir in the management of HIV infection," *HIV/AIDS—Research and Palliative Care*, 1, 31-29 (2009).
Lyle et al., "Benzocycloalkyl amines as novel C-termini for HJIV protease inhibitors," *J. Med. Chem.*, 34(3): 1228-1230 (Mar. 1991).
Majer et al., "Structure-based design and synthesis of inhibitors of a drug resistant mutant of HIV-1 protease," *13th American peptide Symposium*, Edmonton, Canada (1993).
Martinez-Picado et al., "Replicative Fitness of Protease Inhibitor-Resistance Mutants of Human Immunodeficiency Virus Type 1," *J. Virology*, 73(5): 3744-3752 (May 1999).
McQuade et al., "A Synthetic HIV-1 Protease Inhibitor with Antiviral Activity Arrests HIV-Like Particle Maturation," *Science*, 247: 454-456 (1990).
Meek et al., "Inhibition of HIV-1 protease in infected T-lymphocytes by synthetic peptide analogues," *Nature*, 343(6253): 90-92 (Jan. 1990).
Meek, "Inhibitors of HIV-1 Protease," *J. Enzyme Inhibition*, 6(1): 65-98 (Jan. 1992).
Moore et al., "Substrate-based inhibitors of HIV-1 protease," *Perspect. Drug Dis. Design*, 1:85-108 (1993).
Neely et al., "Managing treatment-experienced pediatric and adolescent HIV patients: role of darunavir," *Therapeutics and Clinical Risk Management*, 5, 595-615 (2009).
Norbeck et al., "Hydroxyethyiamine Analogues of the p17/p24 Substrate Cleavage Site are Tight-Binding Inhibitors of HIV Proteases," *J. Med. Chem.*, 33(5): 1285-1288 (May 1990).
Norbeck et al., "HIV Protease Inhibitors," *Ann. Reports Med. Chem.*, 26: 141-150 (1991).
Notice of Motion to Stay, Case 2:10-cv-05956-WHW-MAS, Document 20, Filed Mar. 21, 2011.
Opinion and Order, Case 2:10-cv-05956-WHW-MAS, Document 34, 1-8, Filed May 10, 2011.

(56) References Cited

OTHER PUBLICATIONS

Otto et al., "In vitro isolation and identification of human immunodeficiency virus (HIV) variants with reduced sensitivity to C-2 symmetrical inhibitors of HIV type1 protease," PNAS USA, 90: 7543-7547 (1993).
Plaintiff the Board of Trustees of the University of Illinois's Reply to Defendant Mylan Pharmaceuticals Inc.'s Counterclaims, Case 2:10-cv-05956-WHW-MAS, Document 23, Filed Apr. 11, 2011.
Plaintiff the Board of Trustees of the University of Illinois's Reply to Defendant Lupin Pharmaceuticals, Inc.'s and Lupin Limited's Counterclaims, Case 2:10-cv-05956-WHW-MAS, Document 24, Filed Apr. 11, 2011.
Plaintiffs' Motion to Dismiss Defendant's Counterclaims, Case 2:10-cv-05956-WHW-MAS, Document 29, Filed Apr. 26, 2011.
Plaintiffs' Opposition to Defendants' Motion for a 32-Month Stay, Case 2:10-cv-05956-WHW-MAS, Document 25, Filed Apr. 18, 2011.
Plattner et al., *Drug Discovery Technologies*, Clark et al., eds., Ellish Horwood, Chichester, England: 92-126 (1990).
Ray et al., "Protection of apoptotic cell death by protein A," *Apoptosis*, 5: 509-514 (2000).
Rich et al., "L-687,908, a Potent Hydroxyethylene-Containing HIV Protease Inhibitor," *J. Med. Chem.*, 34(3): 1225-1228 (Mar. 1991).
Roberts et al.,"Rational Design of Peptide-Based HIV Proteinase Inhibitors," *Science*, 248: 358-361 (1990).
Teva Pharmaceuticals USA, Inc.'s Answer and Affirmative Defense to Plaintiffs' Complaint, Case 2:10-cv-01461-WHW-CCC, Document 9, 1-11, Filed May 27, 2011.
Tomasselli et al., "The complexities of AIDS: an assessment of the HIV protease as a therapeutic target," *Int. J. Chem. Biotechnology*, 6: 6-27 (1991).
Turner et al., "Subsite Specificity of Memapsin 2 (β-Secretase): Implications for Inhibitor Design," *Biochemistry*, 40(34): 10001-10006 (Aug. 28, 2001).
Upadhyaya et al., "Molecular analysis of rice ragged stunt oryzavirus segment 9 and sequence conservation among isolates from Thailand and India," *Arch. Virol.*, 140: 1945-1956 (1995).
Vazquez et al., "Inhibitors of HIV-1 Protease Containing the Novel and Potent (R)-(Hydroxyethyl)sulfonamide Isostare," *J. Medicinal Chemistry*, 38(4): 581-584 (Feb. 1995).
Waldholz, Merck's Elation Over AIDS Drug Sours, *Wall Street Journal* (*Eastern Edition*), New York, NY, 85 (Feb. 25, 1994).
Walia et al. "Purification and Characterization of Novel Toxin Produced by *Vibrio cholera* O1," *Infection and Immunity*, 67: 5215-5222 (Oct. 1999).
Wolfe et al., Profile of darunavir in the management of treatment-experienced HIV patients, *HIV/AIDS—Research and Palliative Care*, 1, 13-21 (2009).
Yoshimura et al., "A Potent Human Immunodeficiency Virus Type 1 Protease Inhibitor, UIC-94003 (TMC-126), and Selection of a Novel (A28S) Mutation in the Protease Active Site," *J. Virol.*, 1349-1358 (Feb. 2002).
Adkins, "Amprenavir" *Drugs* (Jun. 1998) 55(6): 837-842.
Moyle, "The role of combinations of HIV protease inhibitors in the management of persons with HIV infection" *Exp. Opin. Invest. Drugs* (1998) 7(3): 413-426.

35

36

37

38

FITNESS ASSAY AND ASSOCIATED METHODS

CROSS-REFERENCE TO RELATED APPLICATIONS

This patent application is a Continuation of U.S. patent application Ser. No. 11/870,931, filed Oct. 11, 2007, which is a Continuation of U.S. patent application Ser. No. 09/720,276, filed Mar. 7, 2001, now U.S. Pat. No. 7,470,506, which is the U.S. National Phase of International Patent Application No. PCT/US1999/014119, filed Jun. 23, 1999, which claims the benefit of U.S. Provisional Patent Application No. 60/090,393, filed Jun. 23, 1998; the disclosures of the '931, '276, '506, '119, and '393 applications are incorporated by reference.

TECHNICAL FIELD OF THE INVENTION

The present invention relates to a biochemical fitness assay and related methods.

BACKGROUND OF THE INVENTION

The development of drug resistance is one of the most perplexing challenges in the field of medicine. One of the most common causes of drug failure in the treatment of diseases involving replicating biological entities, for example, cancer and infectious diseases, is the emergence of drug resistance. One of the most dramatic and tragic examples of drug resistance can be found in connection with the antiviral therapy of acquired immune deficiency syndrome (AIDS).

AIDS is a fatal disease, reported cases of which have increased dramatically within the past several years. Estimates of reported cases in the very near future also continue to rise dramatically.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV will be used herein to refer to HIV viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. For example anti-retroviral agents, such as 3'-azido-2',3'-dideoxythymidine (AZT), 2'3'-dideoxycytidine (ddC), and 2'3'-dideoxyinosine (ddI) are known to inhibit reverse transcriptase. There also exist antiviral agents that inhibit transactivator protein. Nucleoside analogs, such as AZT, are currently available for antiviral therapy. Although very useful, the utility of AZT and related compounds is limited by toxicity and insufficient therapeutic indices for fully adequate therapy.

Retroviral protease inhibitors also have been identified as a class of anti-retroviral agents. Retroviral protease processes polyprotein precursors into viral structural proteins and replicative enzymes. This processing is essential for the assembly and maturation of fully infectious virions. Accordingly, the design of protease inhibitors remains an important therapeutic goal in the treatment of AIDS.

The use of HIV protease inhibitors, in combination with agents that have different antiretroviral mechanisms (e.g., AZT, ddI and ddT), also has been described. For example, synergism against HIV-1 has been observed between certain $C_2$ symmetric HIV inhibitors and AZT (Kageyama et al., *Antimicrob. Agents Chemother.,* 36, 926-933 (1992)).

Numerous classes of potent peptidic inhibitors of protease have been designed using the natural cleavage site of the precursor polyproteins as a starting point. These inhibitors typically are peptide substrate analogs in which the scissile $P_1$—$P_1'$ amide bond has been replaced by a non-hydrolyzable isostere with tetrahedral geometry (Moore et al, *Perspect. Drug Dis. Design,* 1, 85 (1993); Tomasselli et al., *Int. J. Chem. Biotechnology,* 6 (1991); Huff, *J. Med. Chem.,* 34, 2305 (1991); Norbeck et al., *Ann. Reports Med. Chem.,* 26, 141 (1991); and Meek, *J. Enzyme Inhibition,* 6, 65 (1992)). Although these inhibitors are effective in preventing the retroviral protease from functioning, the inhibitors suffer from some distinct disadvantages. Generally, peptidomimetics often make poor drugs, due to their potential adverse pharmacological properties, i.e., poor oral absorption, poor stability and rapid metabolism (Plattner et al, *Drug Discovery Technologies*, Clark et al., eds., Ellish Horwood, Chichester, England (1990)).

The design of the HIV-1 protease inhibitors based on the transition state mimetic concept has led to the generation of a variety of peptide analogs highly active against viral replication in vitro (Erickson et al, *Science,* 249, 527-533 (1990); Kramer et al., *Science,* 231, 1580-1584 (1986); McQuade et al., *Science,* 247, 454-456 (1990); Meek et al., *Nature* (*London*), 343, 90-92 (1990); and Roberts et al., *Science,* 248, 358-361 (1990)). These active agents contain a non-hydrolyzable, dipeptidic isostere, such as hydroxyethylene (McQuade et al., supra; Meek et al., *Nature* (*London*), 343, 90-92 (1990); and Vacca et al., *J. Med. Chem.,* 34, 1225-1228 (1991)) or hydroxyethylamine (Ghosh et al., *Bioorg. Med. Chem. Lett.,* 8, 687-690 (1998); Ghosh et al., *J. Med. Chem.,* 36, 292-295 (1993)); Rich et al., *J. Med. Chem.,* 33, 1285-1288 (1990); and Roberts et al., *Science,* 248, 358-361 (1990)) as an active moiety that mimics the putative transition state of the aspartic protease-catalyzed reaction.

Two-fold ($C_2$) symmetric inhibitors of HIV protease represent another class of potent HIV protease inhibitors, which were created by Erickson et al., on the basis of the three-dimensional symmetry of the enzyme active site (Erickson et al. (1990), supra). Typically, however, the usefulness of currently available HIV protease inhibitors in the treatment of AIDS has been limited by relatively short plasma half-life, poor oral bioavailability, and the technical difficulty of scale-up synthesis (Meek et al. (1992), supra).

In a continuing effort to address the problem of short plasma half-life and poor bioavailability, new HIV protease inhibitors have been identified. For example, HIV protease inhibitors incorporating the 2,5-diamino-3,4-disubstituted-1,6-diphenylhexane isostere are described in Ghosh et al., *Bioorg. Med. Chem. Lett.,* 8, 687-690 (1998) and U.S. Pat. No. 5,728,718 (Randad et al.). HIV protease inhibitors, which incorporate the hydroxyethylamine isostere, are described in U.S. Pat. Nos. 5,502,060 (Thompson et al.), 5,703,076 (Talley et al.), and 5,475,027 (Talley et al.).

Recent studies, however, have revealed the emergence of mutant strains of HIV, in which the protease is resistant to the $C_2$ symmetric inhibitors (Otto et al., *PNAS USA,* 90, 7543 (1993); Ho et al., *J. Virology,* 68, 2016-2020 (1994); and Kaplan et al., *PNAS USA,* 91, 5597-5601 (1994)). In one study, the most abundant mutation found in response to a $C_2$ symmetry based inhibitor was Arg to Gln at position 8 (R8Q), which strongly affects the $S_3/S_3$, subsite of the protease binding domain. In this study, the shortening of the $P_3/P_3$, residues resulted in inhibitors that were equipotent towards both wild-type and R8Q mutant proteases (Majer et al., 13*th American Peptide Symposium*, Edmonton, Canada (1993)). Inhibitors have been truncated to $P_2/P_2$, without significant loss of activity (Lyle et al., *J. Med. Chem.,* 34, 1230 (1991); and Bone et al., *J. Am. Chem. Soc.,* 113, 9382 (1991)). These results suggest that inhibitors can be truncated and yet maintain the crucial interactions necessary for strong binding. The benefits of such an approach include the elimination of two or more peptide bonds, the reduction of molecular weight, and the diminishment of the potential for recognition by degradative enzymes.

More recently, new mutant strains of HIV have emerged that are resistant to multiple, structurally diverse, experimental and chemotherapeutic retroviral protease inhibitors. Such multidrug-resistant HIV strains are typically found in infected patients, who had undergone treatment with a combination of HIV protease inhibitors or a series of different HIV protease inhibitors. The number of reported cases of patients infected with multidrug-resistant HIV is rising dramatically. Tragically for these patients, the available options for AIDS chemotherapy and/or HIV management is severely limited or is, otherwise, completely nonexistent.

Drug resistance is unfortunately the most common reason for drug failures generally. One of the most dramatic examples of drug failure due to resistance is in HIV therapy. Once HIV resistance is obtained to first-line therapy, the chances of future success are greatly diminished because of the development of multidrug cross resistance. Other diseases involving infectious agents (e.g., viruses, bacteria, protozoa, and prions) or other disease-causing cells (e.g., tumor cells) present similar challenges in that drug resistance is a primary cause of drug failure.

In view of the foregoing problems, there exists a need to determine whether a mutant will be capable of replicating in the presence of a drug. There also exists a need for a method of predicting whether drug resistance is likely to emerge in a disease involving a replicating biological entity. There is also a need for a method of devising a long-term therapeutic regimen that minimizes the likelihood that resistance will occur in a disease involving a replicating biological entity. Moreover, there is a need for a method of preventing or inhibiting the development of drug resistance in such diseases.

The present invention provides such methods. These and other advantages of the present invention, as well as additional inventive features, will be apparent from the description of the invention provided herein.

BRIEF SUMMARY OF THE INVENTION

The present invention is predicated on the surprising and unexpected discovery that biochemical "vitality," as described below, can be used to determine the biological fitness of a mutant replicating biological entity relative to its predecessor under the selection pressure of an inhibitor. The present invention provides an assay for determining the biochemical fitness of a biochemical target (i.e., a biomolecule having a biochemical function), of a mutant replicating biological entity relative to its predecessor's biochemical target, in the presence of a compound that acts upon the biochemical target. The assay method of the present invention includes obtaining the predecessor, determining the biochemical vitality of the biochemical target of both the predecessor and the mutant in the presence of a compound that acts upon the biochemical target of the predecessor, and comparing the vitality of the mutant's biochemical target relative to the vitality of the predecessor's biochemical target. Where the biochemical vitality of the mutant is greater than the biochemical fitness of the predecessor, the mutant is predicted to be more biologically fit in the presence of the compound. The assay method can thus be used to predict the emergence of drug resistance for a particular replicating biological entity (e.g., a disease-causing cell) in the presence a drug (e.g., an inhibitor). Utilization of the assay in accordance with the present invention permits the administration of an inhibitor or combination of inhibitors to treat a disease in a way that decreases the likelihood that drug resistance will develop.

The present invention further provides a continuous fluorogenic assay for measuring the anti-HIV protease activity of a protease inhibitor. The continuous fluorogenic assay of the present invention utilizes a substrate of the formula Ala-Arg-Val-Tyr-Phe($NO_2$)-Glu-Ala-Nle-$NH_2$. The continuous fluorogenic assay of the present invention is highly sensitive and particularly useful for the prediction of the antiviral inhibitory activity of a compound against mutant HIV.

The present invention further provides a method of administering a therapeutic compound that inhibits a biochemical target of a disease-causing replicating biological entity. The therapeutic compound, when administered in accordance with the method of the present invention, minimizes the chances that the disease-causing entity will develop drug resistance. As such, the method of administering a therapeutic compound in accordance with the present invention improves the chances of long-term success in therapy.

The present method of administering a therapeutic compound involves the identification of at least one mutant replicating biological entity (the mutant) capable of evolving from the disease-causing replicating biological entity (the predecessor). Biochemical fitness is determined by comparing the biochemical vitality of the mutant's biochemical target with the biochemical vitality of the predecessor's biochemical target. Biochemical fitness is determined in the presence of a drug (e.g, an inhibitor). The biochemical vitality of the mutant's biochemical target is compared to biochemical vitality of the predecessor's biochemical target in the presence of the drug. When there are two or more drugs available for treatment, biochemical fitness can be determined for each drug in accordance with the present invention. A therapeutic compound is then administered from among one of the compounds that produces a lower value for biochemical fitness with respect to one or more mutants. Administration of a therapeutic compound producing a lower fitness value for a particular mutant indicates that the predecessor is less likely to develop resistance in the presence of that compound.

The present invention also provides a method of preventing the development of drug resistance of HIV in an HIV-infected mammal by the administration of a drug resistance-inhibiting effective amount of a compound of the formula:

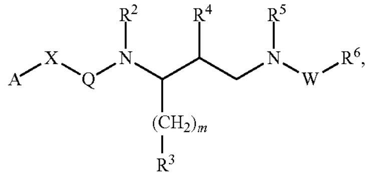

(I)

or a pharmaceutically acceptable salt, a prodrug, or an ester thereof, or a pharmaceutical composition thereof, wherein:

A is a group of the formula:

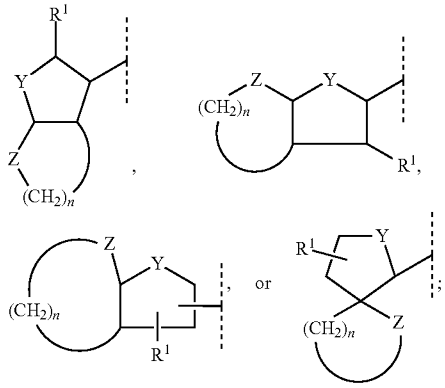

$R^1$ is H or an alkyl, an alkenyl, an alkynyl, a cycloalkyl, a cycloalkylalkyl, an aryl, an aralkyl, a heterocycloalkyl, a heterocycloalkylalkyl, a heteroaryl, or a heteroaralkyl radical, which unsubstituted or substituted;

Y and Z are the same or different and are each selected from the group consisting of CH, O, S, SO, $SO_2$, $NR^8$, $R^8C(O)N$, $R^8C(S)N$, $R^8OC(O)N$, $R^8OC(S)N$, $R^8SC(O)N$, $R^8R^9NC(O)N$, and $R^8R^9NC(S)N$, wherein $R^8$ and $R^9$ are each H, an alkyl, an alkenyl, or an alkynyl;

n is an integer from 1 to 5;

X is a covalent bond, $CHR^{10}$, $CHR^{10}CH_2$, $CH_2CHR^{10}$, O, $NR^{10}$, or S, wherein $R^{10}$ is H, an alkyl, an alkenyl, or an alkynyl;

Q is C(O), C(S), or $SO_2$;

$R^2$ is H, an alkyl, an alkenyl, or an alkynyl;

m is an integer from 0 to 6;

$R^3$ is a cycloalkyl, a heterocycloalkyl, an aryl, or a heteroaryl which is unsubstituted or substituted;

$R^4$ is OH, =O (keto), $NH_2$, or a derivative thereof;

$R^5$ is H, a $C_1$-$C_6$ alkyl radical, a $C_2$-$C_6$ alkenyl radical, or $(CH_2)_qR^{14}$, wherein q is an integer form 0 to 5, and $R^{14}$ is a cycloalkyl, a heterocycloalkyl, an aryl, or a heteroaryl which is unsubstituted or substituted;

W is C(O), C(S), S(O), or $SO_2$; and $R^6$ is a cycloalkyl, heterocycloalkyl, aryl, or heteroaryl which is unsubstituted or substituted. Optionally, $R^5$ and $R^6$, together with the N—W bond of formula (I), comprise a macrocyclic ring which can contain at least one additional heteroatom in the ring skeleton.

DESCRIPTION OF THE PREFERRED EMBODIMENTS

Figure 1:
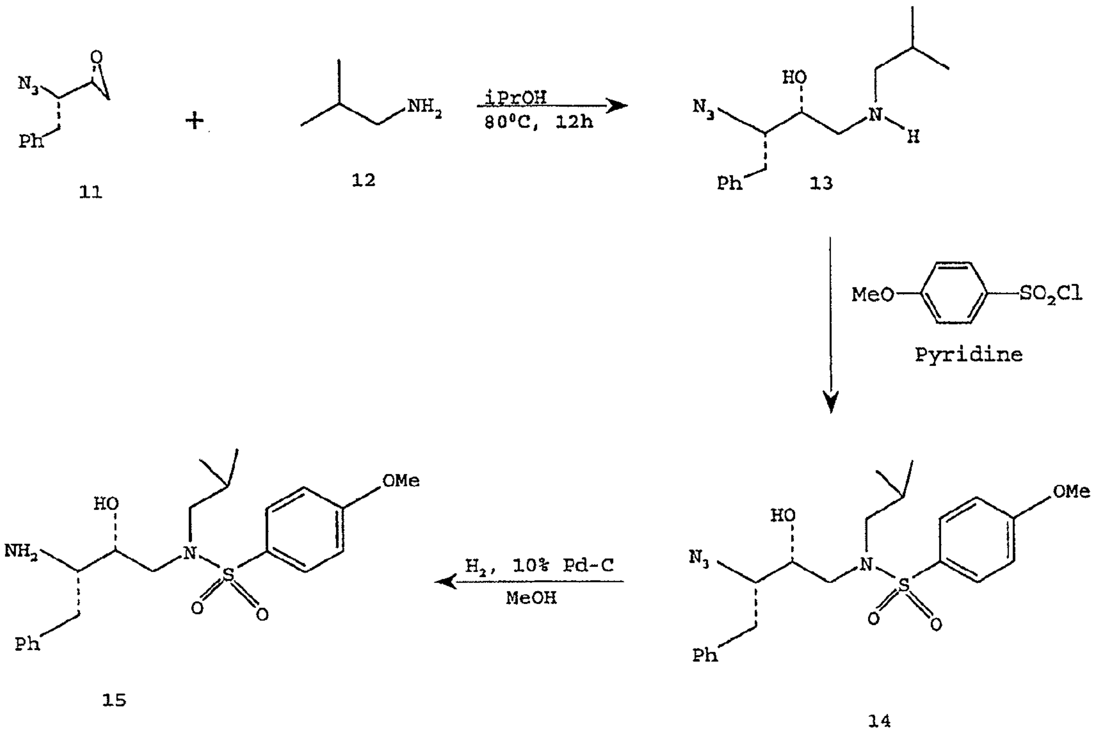
FIG. 1 illustrates the synthesis of a particular sulfonamide isostere core of a compound of the present invention.

The present invention is predicated on the surprising and unexpected discovery to that the "vitality" of a biochemical target of a mutant replicating biological entity relative to that of its predecessor's biochemical target can be used to predict the biological fitness of the mutant under the selection pressure of an inhibitor of the biochemical target. The "vitality" of a biochemical target of a mutant replicating biological entity relative to the "vitality" of its predecessor's biochemical target is defined herein as the "biochemical fitness."

"Vitality" as utilized herein describes the ability of a particular biomolecular "target" (i.e., a biochemical species intended to be inhibited by particular inhibitor) to perform its biochemical function in the presence of the inhibitor. Biochemical vitality is a function of at least two variables: the ability of a particular inhibitor to inhibit a biochemical target of the replicating biological entity in question, and the ability of the cell's biochemical target to inherently perform its biochemical function (irrespective of an inhibitor). Biochemical vitality also can include other factors that effect the ability of a biochemical target to perform its biochemical function in the presence of the inhibitor.

The biochemical target in question can include, for example, a biochemical species with one or more known or unknown biological functions. The biochemical target can be, for example, a biochemical species having one or more specific biochemical function, or it can be a biochemical species that effects or influences a biochemical function directly or indirectly. Suitable biochemical targets include, for example, enzymes, proteins, oligomers, receptors, and the like. Suitable enzymes include, for example, reverse transcriptases, proteases (e.g., retroviral proteases, plasmepsins, and the like), methylases, oxidases, esterases, acyl transferases, and the like. Suitable enzymes also include, for example, viral and non-viral helicases, topoisomerases, DNA gyrases, DNA and RNA polymerases, parasite-encoded proteases, and the like.

Suitable proteins include, for example, proteins that incorporate a conformational change as a major functional requirement, and the like. Examples of such proteins include HIV gp41 and other fusogenic viral proteins and peptides, topoisomerases, and all DNA enzymes, and the like.

Suitable oligomers include, for example, oligomers that require oligomerization in order to perform their biochemical function. Examples of such oligomers include HIV protease, retroviral fusion proteins, peptides, HIV gp 41, viral and non-viral membrane fusion proteins, tumor suppressor proteins (e.g., p53, and the like) prions, ribosomes, and the like.

The ability of a particular inhibitor to inhibit a biochemical target of a particular replicating biological entity can be determined by any suitable method and/or can be obtained from any suitable source. The ability of a particular inhibitor to inhibit a biochemical function of a replicating biological entity can be determined, for example, on the basis of a measurable property, or a measurable relationship of properties, that correlate with the ability of the inhibitor to inhibit the target. Suitable methods for determining the ability of the inhibitor to inhibit the target include, for example, assays, and the like. In some instances, the ability of the inhibitor to inhibit the target can be obtained from one or more suitable sources, for example, assay data from a database, a textbook, or the literature.

When the biochemical target is a protein, the ability of an inhibitor to inhibit the protein can be determined, for example, by obtaining the equilibrium dissociation constant ($K_d$) of drug binding to the target where drug binding interferes with the function of the protein.

When the biochemical target is an enzyme, the ability of an inhibitor to inhibit the enzyme can be determined, for example, by obtaining the inhibition constant ($K_{ith}$), or the like. The inhibition constant can be in terms of drug inhibition constant for the effect of the drug on substrate catalysis (e.g., $K_i$) or dissociation constant for drug binding (e.g., $K_d$) where drug binding correlates with inhibition of enzyme function.

When the biochemical target is an oligomer, the ability of an inhibitor to inhibit the oligomer can be determined, for example, by obtaining the equilibrium dissociation constant ($K_d$) for drug binding where drug binding interferes with oligomerization of the target.

Where the biochemical target is a protein that requires a conformational change for its function, the ability of an inhibitor to inhibit the conformational change can be determined, for example, by obtaining the equilibrium dissociation constant ($K_d$) for drug binding where drug binding interferes with the conformational change of the target.

When the biochemical target is a protein that is required to bind to a ligand, macromolecule, or macromolecular complex to perform its biochemical function, the ability of an inhibitor to inhibit the protein function can be determined by obtaining the equilibrium dissociation constant ($K_d$) for drug binding where drug binding interferes with ligand binding, macromolecule binding, or macromolecular complex binding.

When the biochemical target is a nucleic acid binding protein, the ability of an inhibitor to inhibit the nucleic acid binding protein's function can be determined by obtaining the equilibrium dissociation constant ($K_d$) for drug binding where drug binding interferes with nucleic acid binding.

Vitality also is a function of the biochemical target's ability to inherently perform its biochemical function (irrespective of an inhibitor). The biochemical target's ability to inherently perform its biochemical function can be determined by any suitable method and/or can be obtained from any suitable source. The biochemical target's ability to inherently perform its biochemical function can be determined, for example, on the basis of a measurable property, or measurable relationship of properties, that correlate with the ability of the biochemical target's ability to inherently perform its biochemical function. Suitable methods for determining the biochemical target's ability to inherently perform its biochemical function include, for example, biochemical assays, and the like. In some instances, the ability of a cell's biochemical target to inherently perform its biochemical function can be obtained from one or more suitable sources, for example, assay data from a database, a textbook, or the literature.

When the biochemical target is an enzyme, the ability of the enzyme to inherently perform its biochemical function can be determined, for example, by determining the catalytic efficiency of the enzyme. For example, the catalytic efficiency for enzymes that exhibit Michaelis-Menten kinetics can be determined by obtaining the $k_{cat}/K_M$ ratio, or by a similar method, wherein $k_{cat}$ is the catalytic rate and $K_M$ is the Michaelis constant.

When the biochemical target is a protein, the ability of the protein to inherently perform its biochemical function can be determined, for example, by obtaining the equilibrium constant ($K_{eq}$) for the biochemical function of the protein, or the like.

When the biochemical target is an oligomer, the ability of an inhibitor to perform its biological function can be determined, for example, by obtaining the equilibrium constant ($K_{eq}$) that is associated with oligomerization.

Where the biochemical target is a protein that requires a conformational change for its function, the ability of the target to perform its function can be determined, for example, by obtaining the equilibrium constant ($K_{eq}$) associated with conformational change.

When the biochemical target is a protein that is required to bind to a ligand to perform its function, the ability of the target to perform its function can be determined, for example, by obtaining the equilibrium dissociation constant ($K_d$) for ligand binding.

When the biochemical target is a nucleic acid binding protein, the ability of an inhibitor to perform its function can be determined by obtaining the equilibrium dissociation constant ($K_d$) for nucleic acid binding.

It will be appreciated that vitality also can be a function of other factors that effect the ability of a biochemical target to perform its biochemical function in the presence of the inhibitor. If the biochemical target is a dimeric species, for example, other factors that influence biochemical vitality might include the ability of the species to dimerize in the presence and/or in the absence of the inhibitor. If, by way of example, a mutation causes the dimerization rate to become a factor in the biochemical function of the biochemical target of the mutant relative to its predecessor's, then dimerization rate can be included in the vitality determination.

The biochemical vitalities of a mutant replicating biological entity and its predecessor, when compared, describes the biochemical fitness of the target of the mutant cell. In keeping with the invention, it has been found that the biochemical fitness relates to the biological fitness of the mutant in the presence of the inhibitor. When the value for the biochemical vitality of the target of the mutant exceeds the value for the biochemical vitality of the target of a predecessor of the mutant, the target of the mutant has greater biochemical fitness in the presence of the inhibitor. In such cases, the mutant replicating biological entity is favored over the predecessor and resistance to the inhibitor that is used to treat the predecessor is likely to develop.

Biochemical vitality can be determined in many different ways that suitably relate the various factors relating to the biochemical vitality of the target. For example, a mathematical function may be used to relate the various factors. By way of illustration, when the biochemical target is an enzyme, the vitality can be determined as a function of $K_{inh}$ (e.g., $K_i$ or $K_d$) and enzymatic or catalytic efficiency (e.g., $K_{cat}/K_m$). Vitality can be determined as the product of $K_{inh}$ and enzymatic efficiency, for example, $(K_{inh})\times$(catalytic efficiency), or $(K_i)\times$(catalytic efficiency) or $(K_d)$ (catalytic efficiency). Alternatively, vitality can be determined, for example, as the log of the product of $K_{inh}$ and enzymatic efficiency, for example, log [($K_{inh}$)×(catalytic efficiency)], or log [($K_i$)×(catalytic efficiency)] or log [($K_d$)×(catalytic efficiency)]. Similarly, for enzymes that exhibit Michaelis-Menten kinetics, vitality can be determined as a function of $K_{inh}$ (e.g., $K_i$ or $K_d$) and the $k_{cat}/K_M$ ratio. For example, vitality can be determined as the product of $K_{inh}$ and $k_{cat}/K_M$ e.g., ($K_{inh}$)×($k_{cat}/K_M$), wherein $K_{inh}$ is $K_i$ or $K_d$. Alternatively, vitality can be determined, for example, as the log of the product of $k_{inh}$ and $k_{cat}/K_m$, e.g., log [($K_{inh}$)×($k_{cat}/K_M$)], wherein $K_{inh}$ is $K_i$ or $K_d$. In a preferred embodiment, the biochemical target is an enzyme and the vitality is ($K_i$)×($k_{cat}/K_M$), or log [($K_i$)×($k_{cat}/K_M$)].

"Fitness," unless otherwise indicated, means biochemical fitness. "Biochemical fitness" as utilized herein is a value that represents the vitality of a biochemical target of a mutant replicating biological entity relative to the vitality the biochemical target of its predecessor. Biochemical fitness is determined by comparing the vitality of a biochemical target of a mutant replicating biological entity relative to that of its predecessor. Any suitable comparison of the vitality of a biochemical target of a mutant replicating biological entity relative to that of its predecessor can be used in the determination of fitness. For example, biochemical fitness can be determined as the difference between the biochemical vitality of a biochemical target of a predecessor (biochemical $\text{vitality}_{pred}$) and the biochemical vitality of the biochemical target of a particular mutant replicating biological entity that can evolve from the predecessor (biochemical $\text{vitality}_{mut}$), e.g., (biochemical $\text{vitality}_{mut}$)-(biochemical $\text{vitality}_{pred}$). If biochemical fitness is determined on the basis of this difference, then a positive value indicates that the mutant has a higher fitness relative to its predecessor in the presence of the inhibitor, whereas a negative value indicates that the mutant is less fit relative to its predecessor. A value of zero indicates that the fitness of the mutant and the predecessor are equal. A higher positive value indicates a greater chance that resistance to the inhibitor will emerge, whereas a higher negative value indicates a lower chance that resistance to the inhibitor will emerge.

Alternatively, and preferably, fitness can be determined as the quotient of two biochemical vitalities, for example, as the quotient of a biochemical target of a particular mutant replicating biological entity and the biochemical vitality of the biochemical target of a predecessor, e.g., $$\text{fitness} = \frac{\text{vitality}_{mut}}{\text{vitality}_{pred}}.$$

If fitness is determined on the basis of this quotient, then a value greater than one indicates that the mutant has a higher fitness relative to its predecessor, in the presence of the inhibitor. A value of one indicates that the fitness of the mutant and the predecessor are equal. A value less than one indicates that the mutant is less fit relative to its predecessor. A higher value indicates a greater chance that resistance to the inhibitor/drug will emerge, whereas a lower value indicates a lower chance that resistance to the inhibitor/drug will emerge. A value less than one indicates that the mutant will not emerge in the presence of the inhibitor/drug.

Alternatively, fitness can be determined as the log of the quotient of two biochemical vitalities, for example, as the log of the quotient of a biochemical target of a particular mutant replicating biological entity and the biochemical vitality of the biochemical target of a predecessor, e.g., $$\text{fitness} = \log\left[\frac{\text{vitality}_{mut}}{\text{vitality}_{pred}}\right].$$

If fitness is determined on the basis of this log, then a value greater than zero indicates that the mutant has a higher fitness relative to its predecessor, in the presence of the inhibitor. A negative value indicates that the mutant is less fit relative to its predecessor. A value of zero indicates that the fitness of the mutant and the predecessor are equal. A higher positive value indicates a greater chance that resistance to the inhibitor/drug will emerge, whereas a lower positive value indicates a lower chance that resistance to the inhibitor/drug will emerge. A negative value indicates that the mutant will not emerge in the presence of the inhibitor/drug.

Fitness can be determined in the presence of any suitable compound that inhibits a biochemical target from performing its biological function. The inhibitor, for example, can be a compound that inhibits an enzyme. Suitable enzyme inhibitors include, for example, protease inhibitors, reverse transcriptase inhibitors, DNA polymerase inhibitors, methylase inhibitors, oxidase inhibitors, esterase inhibitors, acyl transferase inhibitors, and the like.

Suitable protease inhibitors include, for example, viral protease inhibitors, plasmepsin inhibitors, and cathepsin D inhibitors. In a preferred embodiment, the inhibitor is a viral protease inhibitor, more preferably a retroviral protease inhibitor, still more preferably an HIV-1 or an HIV-2 protease inhibitor, and most preferably and HIV-1 protease inhibitor. Exemplary HIV-1 protease inhibitors include, for example, saquinavir, ritonavir, indinavir, nelfinavir, amprenavir, and HIV-1 protease inhibitors that are undergoing clinical trials, e.g., tipranavir (PNU-140690).

Suitable plasmepsin inhibitors include, for example, inhibitors of plasmepsin I or II, including inhibitors of plasmepsin I or II that have antimalarial activity. Suitable inhibitors of cathepsin D include, for example, cathepsin D inhibitors that inhibit cathepsin D in primary breast cancer tissues, including cathepsin D inhibitors that inhibit cathepsin D in primary breast cancer tissues and would be expected to lower the risk of metastasis and/or shorter relapse-free survival in breast cancer patients. See, e.g., Gulnik et al., *J. Mol. Biol.,* 227, 265-270 (1992).

Suitable reverse transcriptase inhibitors include, for example, retroviral reverse transcriptase inhibitors, e.g., AZT, 3TC, ddI, ddC, D4T, and the like.

Suitable protein inhibitors include, for example, compounds that inhibit a conformational change in a protein, and the like. Suitable oligomerization inhibitors include, for example, T-20 peptide inhibitor of HIV-1 fusion and other compounds that inhibit oligomers from oligomerizing on a cell surface or within a cell membrane.

In accordance with the present invention, fitness in the presence of an inhibitor can be determined for a biological entity that produces or includes a biological target of the inhibitor. The biological entity is preferably a replicating biological entity, for example, a virus, a parasite, or a cell, preferably a disease-causing cell. Disease-causing replicating biological entities include, for example, tumor cells, cancer cells, and infectious organisms (e.g., fungi, protozoa, bacteria, and the like) and prions.

Cancer cells include, for example, cells associated with breast cancer, colon cancer, lung cancer, and the like. Fitness can be determined for a rapidly growing tumor cell.

Fungi include, for example, *candida albicans*, and the like. Protozoa include, for example, trypanosome species, schistosomial species, malarial protozoa, e.g., *Plasmodium* species. *Plasmodium* species include, for example, *Plasmodium Falciparum, Plasmodium ovale, Plasmodium vivax, Plasmodium malariae*, and the like. Bacteria include, for example, *Helicobacter pylori, Escherichia coli, Salmonella, Streptococcus pyogenes, Staphylococcus aureas, Bacillus anthrax, Mycobacterium tuberculosis, Hemophilus influenza*, and the like. Viruses include, for example, retroviruses (e.g., HIV-1 and HIV-2), herpes viruses, cytomegaloviruses, influenza viruses, epstein-barr virus (EBV), Kaposi's sarcoma herpes virus (KSHV), varicella-zoster virus (VZV), human papillomavirus (HPV), echovirus, picornaviruses, rhinoviruses, poliovirus, coxsackie virus, measles, mumps, human T-cell leukemia virus (HTLV-1), rubella, rotaviruses, yellow fever virus, ebola virus, and other pathogenic viruses, and the like.

Replicating biological entities also include multicellular organisms, for example, infectious microorganisms, e.g., helminths. Helminths include, for example, hookworms (e.g., *ancylostoma duodenale*) *strongyloides stercoralis, fasciola hepatica, trichuris trichiura, trichinella spiralis, taenia solium, taenia saginata*, and the like.

It is believed that drug resistance is the evolutionary result of fitness-based selection of mutant cells/microorganisms in the presence of a drug (or any compound that has biological activity). In accordance with the present invention, the emergence (or non-emergence) of drug resistance in a disease caused by a disease-causing replicating biological entity can be predicted by determining the fitness of a biochemical target of a mutant in the presence of the drug. Thus, the emergence (or non-emergence) of drug resistance can be predicted on the basis of biochemical fitness. While resistance profiles may, in some instances, reflect fitness, it cannot be assumed that the emergence of drug resistance for a particular mutant can be directly predicted on the basis of its resistance profile alone.

The present invention thus provides an assay that can be used to predict the biological fitness of a replicating biological entity in the presence of a particular inhibitor. In a preferred embodiment, an assay is provided for determining the biochemical fitness of a biochemical target of a mutant replicating biological entity relative to its predecessor. In accordance with the assay of the present invention, a predecessor to the mutant is obtained, the biochemical vitality of the biochemical target of the predecessor in the presence of a compound capable of inhibiting the biochemical target of the predecessor is determined, the biochemical vitality of the biochemical target of the mutant in the presence of the compound is determined, and the biochemical vitality of the biochemical target of the mutant relative to the biochemical vitality of the biochemical target of the predecessor are compared.

The assay can be used with a wide variety of infectious microorganisms, as described above, including, for example, a virus, a fungus, a protozoa, or bacterium, a retrovirus, including HIV-1 or HIV-2, and cancer cells. When the infectious microorganism is a protozoa, it is preferably a malarial parasite, which is more preferably a *plasmodium* species.

In another embodiment, the predecessor is a cancer cell, which is preferably a rapidly growing tumor cell, for example, a rapidly growing cancer cell found in breast cancer, colon cancer, lung cancer, a tumor cell of a lymphoid origin, a tumor-derived cell with a high metastatic potential, or the like.

The assay of the present invention can be applied to any suitable biochemical target, preferably a biochemical target whose biochemical vitality can be determined using measurable properties that can be obtained by assay. Desirably, the biochemical target is one that plays an important role in the replication and growth of the entity. By way of example, the biochemical target of the predecessor (and the mutant) can be an enzyme and the compound can be an inhibitor of the enzyme of the predecessor.

The enzyme can be a viral enzyme. Illustrative of viral enzymes are a viral protease enzyme, a viral reverse transcriptase, a viral integrase, a viral polymerase, a viral protein with enzymatic activity, or a retroviral enzyme, including an HIV-1 or an HIV-2 enzyme. Viral protease enzymes, include a retroviral protease, such as an HIV-1 protease or an HIV-2 protease. Viral integrase enzymes include, for example, HIV-1 integrase, HIV-2 integrase, and the like. Viral polymerase can be a retroviral polymerase, including an HIV-1 polymerase or an HIV-2 polymerase. A viral protein with enzymatic activity can be a retroviral protein, such as an HIV-1 protein or an HIV-2 protein.

The enzyme also can be a protozoal enzyme, including a protozoal protease enzyme. The protozoal protease can be a malarial protease. The malarial protease can be a plasmepsin, including plasmepsin I or plasmepsin II. The malarial enzyme can also be a plasmodial enzyme or a protein with enzymatic activity.

In yet another embodiment, the biochemical target of the predecessor is an oligomer and the compound inhibits the oligomerization of the oligomer of the predecessor. In yet another embodiment, the biochemical target of the predecessor is a protein and the compound inhibits a conformational change in the protein of the predecessor.

The biochemical vitality determination can also take into account other factors, preferably measurable factors, that effect the ability of a biochemical target to perform its biochemical function in the presence of the inhibitor. When the biochemical target is an enzyme and the compound is an enzyme inhibitor, the biochemical vitality of the enzyme of the mutant replicating biological entity preferably corresponds to $K_{inh-mut}$, $k_{cat-mut}$, $K_{M-mut}$, and the biochemical vitality of the enzyme of the predecessor preferably corresponds to $K_{inh-pred}$, $k_{cat-pred}$, and $K_{M-pred}$. $K_{inh}$, is an inhibition constant of the compound, $k_{cat}$ is the biochemical catalytic rate, and $K_M$ is the Michaelis constant. More preferably, the vitality of the enzyme corresponds to $K_{inh}$, $k_{cat}$ and $K_M$, and the biochemical vitality of the enzyme of the mutant replicating biological entity is defined by the relationship $K_{inh-mut}(K_{cat-mut}/K_{M-mut})$ (i.e., $(K_{inh-mut})\times(K_{cat-mut}/K_{M-mut})$) and the biochemical vitality of the enzyme of the predecessor is defined by the relationship $K_{inh-pred}(k_{cat-pred}/K_{M-pred})$. The variables $K_{inh-mut}$, $K_{inh-pred}$, $k_{cat-mut}$, $k_{cat-pred}$, $K_{M-mut}$, and $K_{M-pred}$ can be obtained by any suitable means, and are preferably obtained by measurement (e.g., from an assay). When vitality is determined on the basis of these relationships, biochemical fitness in the presence of a given inhibitor/drug preferably is defined by the equation:

$$\frac{K_{inh-mut}(k_{cat-mut}/K_{M-mut})}{K_{inh-pred}(k_{cat-pred}/K_{M-pred})},\text{ or}$$

$$\log\left[\frac{K_{inh-mut}(k_{cat-mut}/K_{M-mut})}{K_{inh-pred}(k_{cat-pred}/K_{M-pred})}\right].$$

$K_{inh}$ can be determined by any suitable means, but typically is determined on the basis of $K_i$ or $K_d$.

The present invention also provides a method of administering a therapeutic compound, which method increases the chances of successful long-term therapy. In a preferred embodiment, the present invention provides a method of administering a therapeutic compound that inhibits a biochemical target of a replicating disease-causing replicating biological entity (disease causing predecessor), including identifying at least one mutant capable of evolving from the disease-causing predecessor. A first biochemical vitality of the biochemical target of the disease-causing predecessor in the presence of a first compound capable of inhibiting the biochemical target of the disease-causing predecessor, and a first biochemical vitality of the biochemical target of the mutant in the presence of the first compound, are determined.

Additional biochemical vitalities of the biochemical target of the disease-causing replicating biological entity in the presence of additional compounds capable of inhibiting the biochemical target of the disease-causing cell, and additional biochemical vitalities of the biochemical target of the mutant in the presence of the additional compounds, are also determined.

Fitnesses in the presence of different inhibitors/drugs can be compared and a therapeutic compound administered on the basis of the comparison. A first biochemical fitness of the biochemical target of the mutant relative to the disease-causing predecessor is determined by comparing the first biochemical vitality of the biochemical target of the mutant with the first biochemical vitality of the biochemical target of the disease-causing predecessor, and a second biochemical fitness of the biochemical target of the mutant relative to the disease-causing replicating biological entity is determined by comparing the second biochemical vitality of the biochemical target of the mutant with the second biochemical vitality of the biochemical target of the disease-causing replicating biological entity. Additional biochemical fitness determinations can be made in the presence of additional compounds. The biochemical fitness values for one or more mutants in the presence of each compound are compared. A therapeutic compound is then administered from among the first and the additional compound(s), which therapeutic compound produces the lowest biochemical fitness values.

In accordance with the method of the present invention, the replicating disease-causing replicating biological entity is less likely to develop resistance in the presence of the therapeutic compound. The therapeutic compound can be administered from among any particular set of compounds, which can have the same biochemical target or different biochemical targets with respect to each other. The method of administering a compound in accordance with the present invention is, therefore, not limited to comparing fitness in the presence of compounds that act on the same biochemical target.

In one embodiment, the disease-causing replicating biological entity is an infectious microorganism, for example, a virus, a fungus, a protozoa, or a bacterium, more preferably a virus or a protozoa. When the infectious microorganism is a virus, it is preferably a retrovirus, which is more preferably HIV-1 or HIV-2, and most preferably HIV-1. When the infectious microorganism is a protozoa, it is preferably a malarial parasite, which is more preferably a *plasmodium* species.

In another embodiment, the disease-causing replicating biological entity is a cancer cell, which is preferably a rapidly growing tumor cell, for example, a rapidly growing cancer cell found in breast cancer, colon cancer, lung cancer, or the like.

The method of administering a compound in accordance with the present invention can be applied to any suitable biochemical target, preferably a biochemical target whose biochemical vitality can be determined using measurable properties that can be obtained by assay. In one embodiment, the biochemical target of the predecessor (and the mutant) is an enzyme and the compound inhibits an enzyme of the predecessor. The enzyme can be any enzyme whose biochemical vitality can be measured including, for example, an enzyme described herein in connection with the fitness assay of the present invention.

In another embodiment, the biochemical target of the disease-causing replicating biological entity is an oligomer and the compound inhibits the oligomerization of the oligomer of the predecessor. In yet another embodiment, the biochemical target of the disease-causing replicating biological entity is a protein and the compound inhibits a conformational change in the protein of the predecessor.

The biochemical vitality can be determined in any suitable manner. For example, vitality can be determined as described herein, e.g., as described in connection with the assay of the present invention.

When an infectious microorganism is tested in accordance with the assay of the present invention, the predecessor can be a wild-type species, or the predecessor can itself be a mutant species. In a particularly preferred embodiment, the predecessor is a retrovirus, which is more preferably a wild-type HIV-1 or HIV-2 strain, most preferably HIV-1. When the predecessor is a wild-type HIV strain, the mutant replicating biological entity preferably has at least one mutation in the biochemical target thereof. When the predecessor has at least one mutation in the biochemical target thereof, the mutant preferably has at least two mutations in the biochemical target thereof.

Similarly, when the method of administering a therapeutic compound in accordance with the present invention is used in connection with an infectious microorganism, the disease-causing replicating biological entity can be a wild-type species, or the disease-causing entity can itself be a mutant species. In a particularly preferred embodiment, the disease-causing replicating biological entity is a retrovirus, which is more preferably a wild-type HIV-1 or HIV-2 strain, most preferably HIV-1. When the disease-causing replicating biological entity is a wild-type HIV strain, the mutant preferably has at least one mutation in the biochemical target thereof. When the disease-causing replicating biological entity has at least one mutation in the biochemical target thereof, the mutant preferably has at least two mutations in the biochemical target thereof.

When the predecessor or the disease-causing replicating biological entity in the assay of the present invention, or in the method of administering a compound in accordance with the present invention, is a wild-type HIV strain, the biochemical target of the mutant preferably has at least one active site mutation. When the predecessor in the assay of the present invention has at least one mutation, and the mutant replicating biological entity has at least two mutations, the biochemical target of the predecessor or of the mutant preferably has at least one active site mutation. When the disease-causing replicating biological entity in the method of the present invention has at least one mutation in the biochemical target thereof, and the mutant has at least two mutations in the biochemical target thereof, the biochemical target of the disease-causing entity or of the mutant preferably has at least one active site mutation.

The present invention further provides a continuous fluorogenic assay for measuring the anti-HIV protease activity of a protease inhibitor, which method comprises adding a solution of HIV protease to a substrate stock solution, in which the substrate has the formula Ala-Arg-Val-Tyr-Phe ($NO_2$)-Glu-Ala-Nle-$NH_2$, to provide a substrate reaction solution. The fluorescence of the substrate reaction solution is then measured at specified time intervals. The solution of HIV protease is then added to a solution of the protease inhibitor and the substrate stock solution, to provide an inhibitor-substrate reaction solution. The fluorescence of the inhibitor-substrate reaction solution is then measured at specified time intervals. The initial velocity of the inhibitor-substrate reaction solution is then calculated by applying the equation:

$$V=V_0/2E_t(\{[K_i(1+S/K_m)+I_t-E_t]^2+4K_i(1+S/K_m)E_t\}^{1/2}-[K_i((1+S/K_m)+I_t-E_t]),$$

wherein V is the initial velocity of the inhibitor reaction solution, $V_0$ is the initial velocity of the substrate reaction solution, $K_m$ is the Michaelis-Menten constant, S is the substrate concentration, $E_t$ is the protease concentration, and $I_t$ is the inhibitor concentration.

The assay method described herein is highly sensitive and particularly useful for the prediction of the antiviral inhibitory activity of a compound against mutant HIV, more particularly multiple mutant HIV, specifically multidrug-resistant human immunodeficiency viruses. The continuous fluorogenic assay of the present invention is distinctly advantageous in that it is more sensitive than standard assays in determining the activity of protease inhibitors against multidrug-resistant HIV. The continuous fluorogenic assay of the present invention is disclosed in more detail in the examples that follow. The inhibitory data obtained in accordance with this continuous fluorogenic assay can be used to determine vitality and fitness for HIV-1 protease in the presence of a protease inhibitor, in accordance with the present invention.

The present invention also provides a method of preventing the emergence of drug resistance in an HIV-infected mammal that includes the administration of a drug resistance-inhibiting effective amount of a compound represented by the formula:

(I)

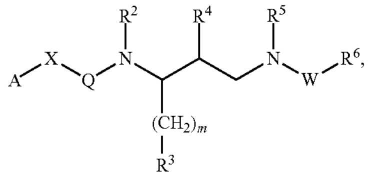

or a pharmaceutically acceptable salt, a prodrug, or an ester thereof, or a pharmaceutical composition thereof, wherein:

A is a group of the formula:

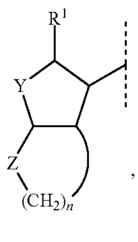

,

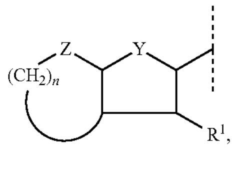

-continued

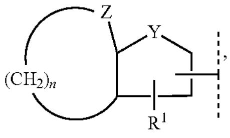

or

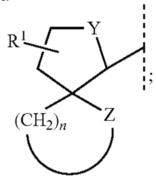

$R^1$ is H or an alkyl, an alkenyl, an alkynyl, a cycloalkyl, a cycloalkylalkyl, an aryl, an aralkyl, a heterocycloalkyl, a heterocycloalkylalkyl, a heteroaryl, or a heteroaralkyl radical, in which at least one hydrogen atom is optionally substituted with a substituent independently selected from the group consisting of $OR^7$, $SR^7$, CN, $NO_2$, $N_3$, and a halogen, wherein $R^7$ is H, an alkyl, an alkenyl, or an alkynyl;

Y and Z are the same or different and are independently selected from the group consisting of CH, O, S, SO, $SO_2$, $NR^8$, $R^8C(O)N$, $R^8C(S)N$, $R^8OC(O)N$, $R^8OC(S)N$, $R^8SC(O)N$, $R^8R^9NC(O)N$, and $R^8R^9NC(S)N$, wherein $R^8$ and $R^9$ are independently selected from the group consisting of H, an alkyl, an alkenyl, and an alkynyl;

n is an integer from 1 to 5;

X is a covalent bond, $CHR^{10}$, $CHR^{10}CH_2$, $CH_2CHR^{10}$, O, $NR^{10}$, or S, wherein $R^{10}$ is H, an alkyl, an alkenyl, or an alkynyl;

Q is C(O), C(S), or $SO_2$;

$R^2$ is H, an alkyl, an alkenyl, or an alkynyl;

m is an integer from 0 to 6;

$R^3$ is a cycloalkyl, a heterocycloalkyl, an aryl, or a heteroaryl in which at least one hydrogen atom is optionally substituted with a substituent independently selected from the group consisting of H, alkyl, $(CH_2)_pR^{11}$, $OR^{12}$, $SR^{12}$, CN, $N_3$, $NO_2$, $NR^{12}R^{13}$, $C(O)R^{12}$, $C(S)R^{12}$, $CO_2R^{12}$, $C(O)SR^{12}$, $C(O)NR^{12}R^{13}$, $C(S)NR^{12}R^{13}$, $NR^{12}C(O)R^{13}$, $NR^{12}C(S)R^{13}$, $NR^{12}CO_2R^{13}$, $NR^{12}C(O)SR^{13}$, and a halogen, wherein:

p is an integer from 0 to 5;

$R^{11}$ is a cycloalkyl, a heterocycloalkyl, an aryl, or a heteroaryl in which at least one hydrogen atom is optionally substituted with a substituent independently selected from the group consisting of a halogen, OH, $OCH_3$, $NH_2$, $NO_2$, SH, and CN; and $R^{12}$ and $R^{13}$ are independently selected from the group consisting of H, an alkyl, an alkenyl, and an alkynyl;

$R^4$ is OH, =O (keto), or $NH_2$, wherein, when $R^4$ is OH, it is optionally in the form of a pharmaceutically acceptable ester or prodrug, and when $R^4$ is $NH_2$, it is optionally an amide, a hydroxylamino, a carbamate, a urea, an alkylamino, a dialkylamino, a protic salt, or a tetraalkylammonium salt;

$R^5$ is H, a $C_1$-$C_6$ alkyl radical, a $C_2$-$C_6$ alkenyl radical, or $(CH_2)_qR^{14}$, wherein q is an integer form 0 to 5, and $R^{14}$ is a cycloalkyl, a heterocycloalkyl, an aryl, or a heteroaryl radical in which at least one hydrogen atom is optionally substituted with a substituent independently selected from the group consisting of a halogen, OH, $OCH_3$, $NH_2$, $NO_2$, SH, and CN;

W is C(O), C(S), S(O), or $SO_2$; and $R^6$ is a cycloalkyl, heterocycloalkyl, aryl, or heteroaryl radical in which at least one hydrogen atom is optionally substituted with a substituent independently selected from the group consisting of a halogen, $OR^{15}$, $SR^{15}$, $S(O)R^{15}$, $SO_2R^{15}$, $SO_2NR^{15}R^{16}$, $SO_2N(OH)R^{15}$, CN, $CR^{15}$=$NR^{16}$, $CR^{15}$=$N(OR^{16})$, $N_3$, $NO_2$, $NR^{15}R^{16}$, $N(OH)R^{15}$, $C(O)R^{15}$, $C(S)R^{15}$, $CO_2R^{15}$, $C(O)SR^{15}$, $C(O)NR^{15}R^{16}$, $C(S)NR^{15}R^{16}$, $C(O)N(OH)R^{15}$, $C(S)N(OH)R^{15}$, $NR^{15}C(O)R^{16}$, $NR^{15}C(S)R^{16}$, $N(OH)C(O)R^{15}$, $N(OH)C(S)R^{15}$, $NR^{15}CO_2R^{16}$, $N(OH)CO_2R^{15}$, $NR^{15}C(O)SR^{16}$, $NR^{15}C(O)NR^{16}R^{17}$, $NR^{15}C(S)NR^{16}R^{17}$, $N(OH)C(O)NR^{15}R^{16}$, $N(OH)C(S)NR^{15}R^{16}$, $NR^{15}C(O)N(OH)R^{16}$, $NR^{15}C(S)N(OH)R^{16}$, $NR^{15}SO_2R^{16}$, $NHSO_2NR^{15}R^{16}$, $NR^{15}SO_2NHR^{16}$, $P(O)(OR^{15})(OR^{16})$, an alkyl, an alkoxy, an alkylthio, an alkylamino, a cycloalkyl, a cycloalkylalkyl, a heterocycloalkyl, a heterocycloalkylalkyl, an aryl, an aryloxy, an arylamino, an arylthio, an aralkyl, an aryloxyalkyl, an arylaminoalkyl, an aralkoxy, an (aryloxy)alkoxy, an (arylamino)alkoxy, an (arylthio)alkoxy, an aralkylamino, an (aryloxy)alkylamino, an (arylamino)alkylamino, an (arylthio)alkylamino, an aralkylthio, an (aryloxy) alkylthio, an (arylamino)alkylthio, an (arylthio)alkylthio, a heteroaryl, a heteroaryloxy, a heteroarylamino, a heteroarylthio, a heteroaralkyl, a heteroaralkoxy, a heteroaralkylamino, and a heteroaralkylthio, wherein $R^{15}$, $R^{16}$, and $R^{17}$ are H, an unsubstituted alkyl, and an unsubstituted alkenyl, wherein, when at least one hydrogen atom of $R^6$ is optionally substituted with a substituent other than a halogen, $OR^{15}$, $SR^{15}$, $S(O)R^{15}$, $SO_2R^{15}$, $SO_2NR^{15}R^{16}$, $SO_2N(OH)R^{15}$, CN, $CR^{15}{=}NR^{16}$, $CR^{15}{=}N(OR^{16})$, $N_3$, $NO_2$, $NR^{15}R^{16}$, $N(OH)R^{15}$, $C(O)R^{15}$, $C(S)R^{15}$, $CO_2R^{15}$, $C(O)SR^{15}$, $C(O)NR^{15}R^{16}$, $C(S)NR^{15}R^{16}$, $C(O)N(OH)R^{15}$, $C(S)N(OH)R^{15}$, $NR^{15}C(O)R^{16}$, $NR^{15}C(S)R^{16}$, $N(OH)C(O)R^{15}$, $N(OH)C(S)R^{15}$, $NR^{15}CO_2R^{16}$, $N(OH)CO_2R^{15}$, $NR^{15}C(O)SR^{16}$, $NR^{15}C(O)NR^{16}R^{17}$, $NR^{15}C(S)NR^{16}R^{17}$, $N(OH)C(O)NR^{15}R^{16}$, $N(OH)C(S)NR^{15}R^{16}$, $NR^{15}C(O)N(OH)R^{16}$, $NR^{15}C(S)N(OH)R^{16}$, $NR^{15}SO_2R^{16}$, $NHSO_2NR^{15}R^{16}$, $NR^{15}SO_2NHR^{16}$, or $P(O)(OR^{15})(OR^{16})$, then at least one hydrogen atom on said substituent is optionally substituted with a halogen, $OR^{15}$, $SR^{15}$, $S(O)R^{15}$, $SO_2R^{15}$, $SO_2NR^{15}R^{16}$, $SO_2N(OH)R^{15}$, CN, $CR^{15}{=}NR^{16}$, $CR^{15}{=}N(OR^{16})$, $N_3$, $NO_2$, $NR^{15}R^{16}$, $N(OH)R^{15}$, $C(O)R^{15}$, $C(S)R^{15}$, $CO_2R^{15}$, $C(O)SR^{15}$, $C(O)NR^{15}R^{16}$, $C(S)NR^{15}R^{16}$, $C(O)N(OH)R^{15}$, $C(S)N(OH)R^{15}$, $NR^{15}C(O)R^{16}$, $NR^{15}C(S)R^{16}$, $N(OH)C(O)R^{15}$, $N(OH)C(S)R^{15}$, $NR^{15}CO_2R^{16}$, $N(OH)CO_2R^{15}$, $NR^{15}C(O)SR^{16}$, $NR^{15}C(O)NR^{16}R^{17}$, $NR^{15}C(S)NR^{16}R^{17}$, $N(OH)C(O)NR^{15}R^{16}$, $N(OH)C(S)NR^{15}R^{16}$, $NR^{15}C(O)N(OH)R^{16}$, $NR^{15}C(S)N(OH)R^{16}$, $NR^{15}SO_2R^{16}$, $NHSO_2NR^{15}R^{16}$, $NR^{15}SO_2NHR^{16}$, or $P(O)(OR^{15})(OR^{16})$.

Optionally, $R^5$ and $R^6$ are covalently bonded such that $R^5$ and $R^6$, together with the N—W bond of formula (I), comprise a 12 to 18 membered ring. The 12 to 18 membered ring can comprise at least one additional heteroatom in the ring skeleton other than the nitrogen of the N—W bond (e.g., N, O, or S) within the ring. In the practice of the method of preventing the emergence of drug resistance in an HIV-infected mammal, it is preferable that a mutant virus that is capable of evolving from the infection has low fitness, relative to the infecting virus, in the presence of the compound or combination of compounds that are administered.

As utilized herein, the term "alkyl" means a straight-chain or branched alkyl radical containing from about 1 to about 20 carbon atoms chain, preferably from about 1 to about 10 carbon atoms, more preferably from about 1 to about 8 carbon atoms, still more preferably from about 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "alkenyl" means a straight-chain or branched-chain alkenyl radical having one or more double bonds and containing from about 2 to about 20 carbon atoms chain, preferably from about 2 to about 10 carbon atoms, more preferably from about 2 to about 8 carbon atoms, still more preferably from about 2 to about 6 carbon atoms. Examples of such substituents include vinyl, allyl, 1,4-butadienyl, isopropenyl, and the like.

The term "alkynyl" means a straight-chain or branched-chain alkynyl radical having one or more triple bonds and containing from about 2 to about 20 carbon atoms chain, preferably from about 2 to about 10 carbon atoms, more preferably from about 2 to about 8 carbon atoms, still more preferably from about 2 to about 6 carbon atoms. Examples of such radicals include ethynyl, propynyl(propargyl), butynyl, and the like.

The term "alkoxy" means an alkyl ether radical, wherein the term "alkyl" is defined as above. Examples of alkoxy radicals include methoxy, ethoxy, n-propoxy, isopropoxy, n-butoxy, isobutoxy, sec-butoxy, tert-butoxy, hexanoxy, and the like.

The term "alkylthio" means an alkyl thioether radical, wherein the term "alkyl" is defined as above. Examples of alkylthio radicals include methylthio ($SCH_3$), ethylthio ($SCH_2CH_3$), n-propylthio, isopropylthio, n-butylthio, isobutylthio, sec-butylthio, tert-butylthio, n-hexylthio, and the like.

The term "alkylamino" means an alkyl amine radical, wherein the term "alkyl" is defined as above. Examples of alkylamino radicals include methylamino ($NHCH_3$), ethylamino ($NHCH_2CH_3$), n-propylamino, isopropylamino, n-butylamino, isobutylamino, sec-butylamino, tert-butylamino, n-hexylamino, and the like.

The term "cycloalkyl" means a monocyclic or a polycyclic alkyl radical defined by one or more alkyl carbocyclic rings, which can be the same or different when the cycloalkyl is a polycyclic radical having 3 to about 10 carbon atoms in the carbocyclic skeleton in each ring, preferably about 4 to about 7 carbon atoms, more preferably 5 to 6 carbons atoms. Examples of monocyclic cycloalkyl radicals include cyclopropyl, cyclobutyl, cyclopentyl, cyclohexyl, cycloheptyl, cyclodecyl, and the like. Examples of polycyclic cycloalkyl radicals include decahydronaphthyl, bicyclo[5.4.0]undecyl, adamantyl, and the like.

The term "cycloalkylalkyl" means an alkyl radical as defined herein, in which at least one hydrogen atom on the alkyl radical is replaced by a cycloalkyl radical as defined herein. Examples of cycloalkylalkyl radicals include cyclohexylmethyl, 3-cyclopentylbutyl, and the like.

The term "heterocycloalkyl" means a cycloalkyl radical as defined herein (including polycyclics), wherein at least one carbon which defines the carbocyclic skeleton is substituted with a heteroatom such as, for example, O, N, or S, optionally comprising one or more double bond within the ring, provided the ring is not heteroaryl as defined herein. The heterocycloalkyl preferably has 3 to about 10 atoms (members) in the carbocyclic skeleton of each ring, preferably about 4 to about 7 atoms, more preferably 5 to 6 atoms. Examples of heterocycloalkyl radicals include epoxy, aziridyl, oxetanyl, tetrahydrofuranyl, dihydrofuranyl, piperadyl, piperidinyl, pyperazyl, piperazinyl, pyranyl, morpholinyl, and the like.

The term "heterocycloalkylalkyl" means an alkyl radical as defined herein, in which at least one hydrogen atom on the alkyl radical is replace by a heterocycloalkyl radical as defined herein. Examples of heterocycloalkylalkyl radicals include 2-morpholinomethyl, 3-(4-morpholino)-propyl, 4-(2-tetrahydrofuranyl)-butyl, and the like.

The term "aryl" refers to an aromatic carbocyclic radical, as commonly understood in the art, and includes monocyclic and polycyclic aromatics such as, for example, phenyl and naphthyl radicals, optionally substituted with one or more substituents selected from the group consisting of a halogen, an alkyl, alkoxy, amino, cyano, nitro, and the like.

The term "aryloxy" means aryl as defined herein, wherein a hydrogen atom is replaced by an oxygen. Examples of aryloxy radicals include phenoxy, naphthoxy, 4-fluorophenoxy, and the like.

The term "arylamino" means aryl as defined herein, wherein a hydrogen atom is replaced by an amine. Examples of arylamino radicals include phenylamino, naphthylamino, 3-nitrophenylamino, 4-aminophenylamino, and the like.

The term "arylthio" means aryl as defined herein, wherein a hydrogen atom is replaced by a sulfur atom. Examples of arylthio radicals include phenylthio, naphthylthio, 3-nitrophenylthio, 4-thiophenylthio, and the like.

The term "aralkyl" means alkyl as defined herein, wherein an alkyl hydrogen atom is replaced by an aryl as defined herein. Examples of aralkyl radicals include benzyl, phenethyl, 3-(2-naphthyl)-butyl, and the like.

The term "aryloxyalkyl" means alkyl as defined herein, wherein an alkyl hydrogen atom is replaced by an aryloxy as defined herein. Examples of aryloxyalkyl radicals include phenoxyethyl, 4-(3-aminophenoxy)-1-butyl, and the like.

The term "arylaminoalkyl" means alkyl as defined herein, wherein an alkyl hydrogen atom is replaced by an arylamino as defined herein. Examples of arylaminoalkyl radicals include phenylaminoethyl, 4-(3-methoxyphenylamino)-1-butyl, and the like.

The term "aralkoxy" means alkoxy as defined herein, wherein an alkyl hydrogen atom is replaced by an aryl as defined herein. Examples of aralkoxy radicals include 2-phenylethoxy, 2-phenyl-1-propoxy, and the like.

The term "(aryloxy)alkoxy" means alkoxy as defined herein, wherein an alkyl hydrogen atom is replaced by an aryloxy as defined herein. Examples of (aryloxy)alkoxy radicals include 2-phenoxyethoxy, 4-(3-aminophenoxy)-1-butoxy, and the like.

The term "(arylamino)alkoxy" means alkoxy as defined herein, wherein an alkyl hydrogen atom is replaced by an arylamino as defined herein. Examples of (arylamino)alkoxy radicals include 2-(phenylamino)-ethoxy, 2-(2-naphthylamino)-1-butoxy, and the like.

The term "(arylthio)alkoxy" means alkoxy as defined herein, wherein an alkyl hydrogen atom is replaced by an arylthio as defined herein. Examples of (arylthio)alkoxy radicals include 2-(phenylthio)-ethoxy, and the like.

The term "aralkylamino" means alkylamino as defined herein, wherein an alkyl hydrogen atom is replaced by an aryl as defined herein. Examples of aralkylamino radicals include 2-phenethylamino, 4-phenyl-n-butylamino, and the like.

The term "(aryloxy)alkylamino" means alkylamino as defined herein, wherein an alkyl hydrogen atom is replaced by an aryloxy as defined herein. Examples of (aryloxy)alkylamino radicals include 3-phenoxy-n-propylamino, 4-phenoxybutylamino, and the like.

The term "(arylamino)alkylamino" means alkylamino as defined herein, wherein an alkyl hydrogen atom is replaced by an arylamino as defined herein. Examples of (arylamino)alkylamino radicals include 3-(naphthylamino)-1-propylamino, 4-(phenylamino)-1-butylamino, and the like.

The term "(arylthio)alkylamino" means alkylamino as defined herein, wherein an alkyl hydrogen atom is replaced by an arylthio as defined herein. Examples of (arylthio)alkylamino radicals include 2-(phenylthio)-ethylamino, and the like.

The term "aralkylthio" means alkylthio as defined herein, wherein an alkyl hydrogen atom is replaced by an aryl as defined herein. Examples of aralkylthio radicals include 3-phenyl-2-propylthio, 2-(2-naphthyl)-ethylthio, and the like.

The term "(aryloxy)alkylthio" means alkylthio as defined herein, wherein an alkyl hydrogen atom is replaced by an aryloxy as defined herein. Examples of (aryloxy)alkylthio radicals include 3-phenoxypropylthio, 4-(2-fluorophenoxy)-butylthio, and the like.

The term "(arylamino)alkylthio" means alkylthio as defined herein, wherein an alkyl hydrogen atom is replaced by an arylamino as defined herein. Examples of (arylamino)alkylthio radicals include 2-(phenylamino)-ethylthio, 3-(2-naphthylamino)-n-propylthio, and the like.

The term "(arylthio)alkylthio" means alkylthio as defined herein, wherein an alkyl hydrogen atom is replaced by an arylthio as defined herein. Examples of (arylthio)alkylthio radicals include 2-(naphthylthio)-ethylthio, 3-(phenylthio)-propylthio, and the like.

The term "heteroaryl" means a radical defined by an aromatic heterocyclic ring as commonly understood in the art, including monocyclic radicals such as, for example, imidazole, thiazole, pyrazole, pyrrole, furane, pyrazoline, thiophene, oxazole, isoxazol, pyridine, pyridone, pyrimidine, pyrazine, and triazine radicals, and also including polycyclics such as, for example, quinoline, isoquinoline, indole, and benzothiazole radicals, which heteroaryl radicals are optionally substituted with one or more substituents selected from the group consisting of a halogen, an alkyl, alkoxy, amino, cyano, nitro, and the like. It will be appreciated that the heterocycloalkyl and heteroaryl substituents can be coupled to the compounds of the present invention via a heteroatom, such as nitrogen (e.g., 1-imidazolyl).

The term "heteroaryloxy" means heteroaryl as defined herein, wherein a hydrogen atom on the heteroaryl ring is replaced by an oxygen. Heteroaryloxy radicals include, for example, 4-pyridyloxy, 5-quinolyloxy, and the like.

The term "heteroarylamino" means heteroaryl as defined herein, wherein a hydrogen atom on the heteroaryl ring is replaced by an nitrogen. Heteroarylamino radicals include, for example, 4-thiazolylamino, 2-pyridylamino, and the like.

The term "heteroarylthio" means heteroaryl as defined herein, wherein a hydrogen atom on the heteroaryl ring is replaced by a sulfur. Heteroarylthio radicals include, for example, 3-pyridylthio, 3-quinolylthio, 4-imidazolylthio, and the like.

The term "heteroaralkyl" means alkyl as defined herein, wherein an alkyl hydrogen atom is replaced by a heteroaryl as defined herein. Examples of heteroaralkyl radicals include 2-pyridylmethyl, 3-(4-thiazolyl)-propyl, and the like.

The term "heteroaralkoxy" means alkoxy as defined herein, wherein an alkyl hydrogen atom is replaced by a heteroaryl as defined herein. Examples of heteroaralkoxy radicals include 2-pyridylmethoxy, 4-(1-imidazolyl)-butoxy, and the like.

The term "heteroaralkylamino" means alkylamino as defined herein, wherein an alkyl hydrogen atom is replaced by a heteroaryl as defined herein. Examples of heteroaralkylamino radicals include 4-pyridylmethylamino, 3-(2-furanyl)-propylamino, and the like.

The term "heteroaralkylthio" means alkylthio as defined herein, wherein an alkyl hydrogen atom is replaced by a heteroaryl as defined herein. Examples of heteroaralkylthio radicals include 3-pyridylmethylthio, 3-(4-thiazolyl)-propylthio, and the like.

In the compound of Formula I, A is preferably a group of the formula:

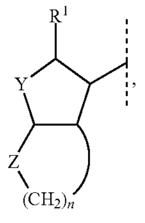

$R^1$ is H or an alkyl, an alkenyl, a cycloalkyl, a cycloalkylalkyl, an aryl, an aralkyl, a heterocycloalkyl, a heterocycloalkylalkyl, a heteroaryl, or a heteroaralkyl radical, in which at least one hydrogen atom is optionally substituted with a substituent independently selected from the group consisting of $OR^7$, $SR^7$, CN, $NO_2$, $N_3$, and a halogen, wherein $R^7$ is H, an unsubstituted alkyl, or an unsubstituted alkenyl; Y and Z are the same or different and are independently selected from the group consisting of $CH_2$, O, S, SO, $SO_2$, $NR^8$, $R^8C(O)N$, $R^8C(S)N$, $R^8OC(O)N$, $R^8OC(S)N$, $R^8SC(O)N$, $R^8R^9NC(O)N$, and $R^8R^9NC(S)N$, wherein $R^8$ and $R^9$ are independently selected from the group consisting of H, an unsubstituted alkyl, and an unsubstituted alkenyl; X is a covalent bond, $CHR^{10}$, $CHR^{10}CH_2$, $CH_2CHR^{10}$, O, $NR^{10}$, or S, wherein $R^{10}$ is H, an unsubstituted alkyl, or an unsubstituted alkenyl; $R^2$ is H, a $C_1$-$C_6$alkyl radical, or a $C_2$-$C_6$ alkenyl radical; $R^{12}$ and $R^{13}$, as defined with respect to $R^3$, are independently selected from the group consisting of H, an unsubstituted alkyl, and an unsubstituted alkenyl radical; $R^4$ is OH, $NH_2$, or $NHCH_3$; W is C(O), C(S), or $SO_2$; and $R^6$ is a cycloalkyl, heterocycloalkyl, aryl, or heteroaryl radical in which at least one hydrogen atom is optionally substituted with a substituent independently selected from the group consisting of a halogen, $OR^{15}$, $SR^{15}$, CN, $N_3$, $NO_2$, $NR^{15}R^{16}$, $C(O)R^{15}$, $C(S)R^{15}$, $CO_2R^{15}$, $C(O)SR^{15}$, $C(O)NR^{15}R^{16}$, $C(S)NR^{15}R^{16}$, $NR^{15}C(O)R^{16}$, $NR^{15}C(S)R^{16}$, $NR^{15}CO_2R^{16}$, $NR^{15}C(O)SR^{16}$, $NR^{15}C(O)NR^{16}R^{17}$, and $NR^{15}C(S)NR^{16}R^{17}$, an alkyl, an alkoxy, an alkylthio, an alkylamino, a cycloalkyl, a cycloalkylalkyl, a heterocycloalkyl, a heterocycloalkylalkyl, an aryl, an aryloxy, an arylamino, an arylthio, an aralkyl, an aryloxyalkyl, an arylaminoalkyl, an aralkoxy, an (aryloxy)alkoxy, an (arylamino)alkoxy, an (arylthio)alkoxy, an aralkylamino, an (aryloxy)alkylamino, an (arylamino)alkylamino, an (arylthio) alkylamino, an aralkylthio, an (aryloxy)alkylthio, an (arylamino)alkylthio, an (arylthio)alkylthio, a heteroaryl, a heteroaryloxy, a heteroarylamino, a heteroarylthio, a heteroaralkyl, a heteroaralkoxy, a heteroaralkylamino, and a heteroaralkylthio, wherein $R^{15}$, $R^{16}$, and $R^{17}$ are H, an unsubstituted alkyl, and an unsubstituted alkenyl, such that when at least one hydrogen atom of $R^6$ is optionally substituted with a substituent other than a halogen, $OR^{15}$, $SR^{15}$, CN, $N_3$, $NO_2$, $NR^{15}R^{16}$, $C(O)R^{15}$, $C(S)R^{15}$, $CO_2R^{15}$, $C(O)SR^{15}$, $C(O)NR^{15}R^{16}$, $C(S)NR^{15}R^{16}$, $NR^{15}C(O)R^{16}$, $NR^{15}C(S)R^{16}$, $NR^{15}CO_2R^{16}$, $NR^{15}C(O)SR^{16}$, $NR^{15}C(O)NR^{16}R^{17}$, or $NR^{15}C(S)NR^{16}R^{17}$, at least one hydrogen atom on said substituent attached to $R^6$ is optionally substituted with a halogen, $OR^5$, $SR^{15}$, CN, $N_3$, $NO_2$, $NR^{15}R^{16}$, $C(O)R^{15}$, $C(S)R^{15}$, $CO_2R^{15}$, $C(O)SR^{15}$, $C(O)NR^{15}R^{16}$, $C(S)NR^{15}R^{16}$, $NR^{15}C(O)R^{15}$, $NR^{15}C(S)R^{16}$, $NR^{15}CO_2R^{16}$, $NR^{15}C(O)SR^{16}$, $NR^{15}C(O)NR^{16}R^{17}$, or $NR^{15}C(S)NR^{16}R^{17}$.

It is further preferred that when $R^1$ is an alkyl or an alkenyl radical (i.e., an alkyl or an alkenyl substituent), then it is a $C_1$-$C_6$ alkyl or, in the case when $R^1$ is an alkenyl, it is a $C_2$-$C_6$ alkenyl. When $R^1$ is a monocyclic substituent such as, for example, a cycloalkyl, a heterocycloalkyl, an aryl, or a heteroaryl, it preferably comprises 4-7 members in the ring that defines the monocyclic skeleton. When $R^7$, $R^8$ or $R^9$ is an unsubstituted alkyl, it is preferably a $C_1$-$C_6$ unsubstituted alkyl; and when $R^7$, $R^8$ or $R^9$ is an unsubstituted alkenyl, it is preferably a $C_2$-$C_6$ unsubstituted alkenyl. The ring defined by $R^3$ preferably comprises 4-7 members or, in the case of polycyclics, each ring comprises 4-7 members. When $R^3$ is $(CH_2)_pR^{11}$, the ring defined by $R^{11}$ preferably comprises 4-7 members, or, in the case of polycyclics, each ring comprises 4-7 members. When either of $R^{12}$ or $R^{13}$ is an unsubstituted alkyl, it is preferably a $C_1$-$C_6$ unsubstituted alkyl, and when either of $R^{12}$ or $R^{13}$ is an unsubstituted alkenyl, it is a $C_2$-$C_6$ unsubstituted alkyl. When $R^{14}$ is a cycloalkyl, a heterocycloalkyl, an aryl, or a heteroaryl, the ring defined by $R^{14}$ preferably comprises 4-7 members, or, in the case of polycyclics, each ring comprises 4-7 members. When $R^6$ is a cycloalkyl, a heterocycloalkyl, aryl, or a heteroaryl, the ring defined by $R^6$ preferably comprises 4-7 members, or, in the case of polycyclics, each ring comprises 4-7 members, and when $R^6$ is substituted with a substituent that is an alkyl, an alkylthio, or an alkylamino, it is preferred that the substituent comprises from one to six carbon atoms, and when $R^6$ is substituted with a substituent that is a cycloalkyl, a heterocycloalkyl, an aryl, or a heteroaryl, the ring defined by the substituent preferably comprises 4-7 members or, in the case of polycyclics, each ring comprises 4-7 members.

In a preferred embodiment, the method of preventing the emergence of resistance in accordance with the present invention includes administering a compound of Formula (I), wherein Q is C(O), $R^2$ is H, and W is C(O) or $SO_2$. In a further preferred embodiment, Q is C(O), $R^2$ is H, $R^4$ is OH, W is $SO_2$, and the stereochemical orientation of the asymmetric centers is represented by formula (IA) or (IB) below:

(IA)

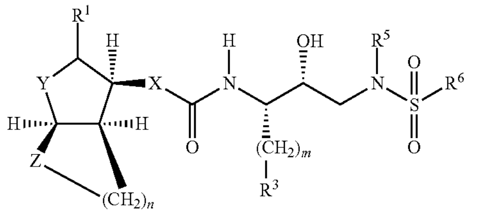

or (IB)

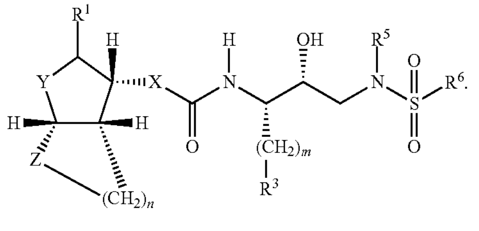

It is further preferred that $R^6$ is a monocyclic substituent, preferably an aromatic ring, which is preferably a substituted benzene ring, as illustrated by the formula:

(IC)

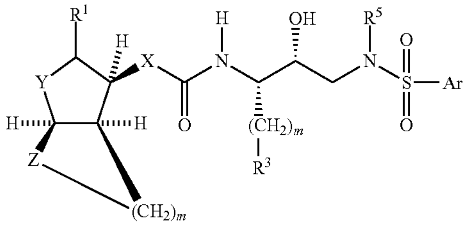

or (ID)

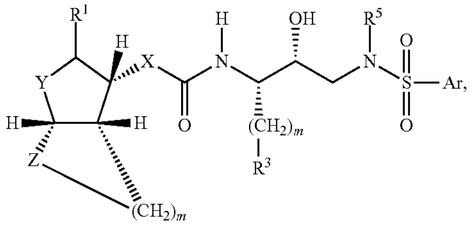

wherein Ar is a phenyl which is optionally substituted with a substituent selected from the group consisting of methyl, amino, hydroxy, methoxy, methylthio, hydroxymethyl, aminomethyl, and methoxymethyl.

In a preferred series, Y and Z are oxygen atoms, n is 2, the resulting bis-tetrahydrofuranyl ring system has the stereochemical orientations illustrated in Formulae (IC) and (ID) above, m is 1, and $R^3$ is phenyl, in which case the compound is represented by the formula:

(IE)

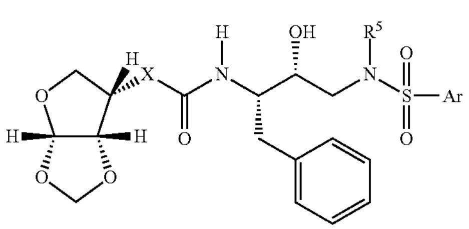

or (IF)

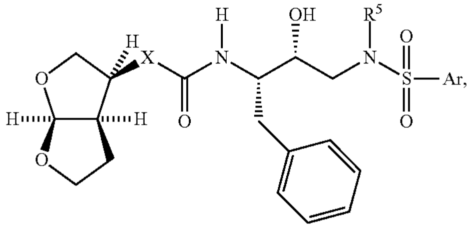

wherein Ar is a phenyl which is optionally substituted with a substituent selected from the group consisting of methyl, amino, hydroxy, methoxy, methylthio, hydroxymethyl, aminomethyl, and methoxymethyl. When the compound is a compound of Formula (IE) or (IF), wherein at least one hydrogen atom on Ar substituted with a substituent selected from the group consisting of methyl, amino, hydroxy, methoxy, methylthio, hydroxymethyl, and methoxymethyl, it is further preferred that X is an oxygen. Still more preferably, X is an oxygen and $R^5$ is isobutyl. Suitable Ar substituents include phenyl groups that are substituted at the para position, the meta position, and/or the ortho position. Examples of suitable Ar substituents are shown in Table 4, and in FIGS. 3 and 5A-5D.

A resistance-inhibiting effective amount is an amount sufficient to produce an in vivo drug concentration or level in which the biochemical vitality of a mutant HIV is lower than the biochemical vitality of the HIV (predecessor) infecting the HIV-infected mammal. For example, a resistance-inhibiting effective amount is an amount sufficient to produce an in vivo drug concentration or level where the value for biochemical fitness is less than one, when determined by the ratio of the biochemical vitality of the mutant to the biochemical vitality of the predecessor. The compound can be administered to a wild-type HIV-infected mammal to prevent the emergence of first line resistance, or it can be administered to a mammal infected with a mutant-HIV to prevent the emergence of drug resistance due to further mutations.

The compound is preferably administered in the form of a pharmaceutical composition. The pharmaceutical composition preferably includes a pharmaceutically acceptable carrier and a resistance-inhibiting effective amount of at least one of the aforesaid compound, alone or in combination with another antiretroviral compound such as, for example, a wild-type HIV protease inhibitor, a mutant HIV retroviral protease inhibitor, or a reverse transcriptase inhibitor. Generally, the pharmaceutical composition of the present invention comprises a resistance-inhibiting effective amount of at least one compound of Formula (I), as disclosed herein, and a pharmaceutically acceptable carrier.

In a preferred embodiment, a pharmaceutical composition is administered that comprises a resistance-inhibiting effective amount of at least one compound of Formula (IA) or Formula (IB), or a pharmaceutically acceptable salt, prodrug, or ester thereof, and a pharmaceutically acceptable carrier. In a further preferred embodiment, the pharmaceutical composition comprises a resistance-inhibiting effective amount of at least one compound of Formula (IC) or Formula (ID), or a pharmaceutically acceptable salt, prodrug, or ester thereof, and a pharmaceutically acceptable carrier. In a highly preferred embodiment, the pharmaceutical composition comprises a resistance-inhibiting effective amount of at least one compound of Formula (IE), and pharmaceutically acceptable salts, prodrugs, and esters thereof, and a pharmaceutically acceptable carrier.

Pharmaceutically acceptable carriers are well-known to those of skill in the art. The choice of a carrier will be determined in part by the particular composition, as well as by the particular mode of administration. Accordingly, there are a wide variety of suitable formulations for administration in accordance the present invention.

The pharmaceutical composition may be administered in a form suitable for oral use such as, for example, tablets, troches, lozenges, aqueous or oily suspensions or solutions, dispersible powders or granules, emulsions, hard or soft capsules, syrups or elixirs. Compositions intended for oral use may be prepared according to any method known in the art form the manufacture of pharmaceutical compositions, and such compositions can contain one or more agents such as, for example, sweetening agents, flavoring agents, coloring agents, and preserving agents in order to provide a pharmaceutically elegant and/or palatable preparation. Tablets can contain the active ingredient in admixture with non-toxic pharmaceutically acceptable excipients which are suitable for manufacture of tablets. Such excipients can be, for example, inert diluents such as, for example, calcium carbonate, lactose, calcium phosphate or sodium phosphate; granulating and disintegrating agents such as, for example, maize starch or alginic acid; binding agents such as, for example, starch, gelatine or acacia, and lubricating agents such as, for example, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use also can be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example arachis oil, peanut oil, liquid paraffin or olive oil.

Aqueous suspensions typically contain the active materials in admixture with excipients suitable for the manufacture of aqueous suspensions. Such excipients are suspending agents, for example, sodium carboxymethyl cellulose, methylcellulose, hydroxypropylmethylcellulose, sodium alginate, polyvinylpyrrolidone, gum tragacanth and gam acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan mono-oleate. The aqueous suspensions also can contain one or more preservatives, for example, ethyl or n-propyl p-hydroxy benzoate, one or more coloring agents, one or more flavoring agents and one or more sweetening agents such as, for example, sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavoring agents may be added to provide a palatable oral preparation. These compositions can be preserved by the addition of an antioxidant such as, for example, ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, also may be present.

The pharmaceutical composition also can be administered in the form of oil-in-water emulsions. The oily phase can be a vegetable oil, for example, olive oil or arachis oils, or a mineral oil, for example liquid paraffin or mixtures of these. Suitable emulsifying agents may be naturally-occurring gums, for example gum acacia or gum tragacantn, naturally-occurring phosphatides, for example soya bean lecithin, and esters or partial esters derived from fatty acids and hexitol anhydrides, for example sorbitan mono-oleate, and condensation products of the said partial esters and ethylene oxide, for example polyoxyethylene sorbitan mono-oleate. The emulsions also can contain sweetening and flavoring agents.

The pharmaceutical composition also can be administered in the form of syrups and elixirs, which are typically formulated with sweetening agents such as, for example, glycerol, sorbitol or sucrose. Such formulations also can contain a demulcent, a preservative and flavoring and coloring agents.

Further, the pharmaceutical composition can be administered in the form of a sterile injectable preparation, for example, as a sterile injectable aqueous or oleagenous suspension. Suitable suspensions for parenteral administration can be formulated according to the known art using those suitable dispersing or wetting agents and suspending agents which have been mentioned above. Formulations suitable for parenteral administration include, for example, aqueous and non-aqueous, isotonic sterile injection solutions, which can contain anti-oxidants, buffers, bacteriostates, and solutes that render the formulation isotonic with the blood of the intended recipient, and aqueous and non-aqueous sterile suspensions that can include suspending agents, solubilizers, thickening agents, stabilizers, and preservatives. The sterile injectable preparation can be a solution or a suspension in a non-toxic parenterally-acceptable diluent or solvent, for example, as a solution in water or 1,3-butanediol. Among the acceptable vehicles and solvents that can be employed, for example, are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as, for example, oleic acid find use in the preparation of injectables.

Further, the compound can be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols. Formulations suitable for vaginal administration can be presented as pessaries, tampons, creams, gels, pastes, and foams.

Formulations suitable for topical administration may be presented as creams, gels, pastes, or foams, containing, in addition to the active ingredient, such carriers as are known in the art to be appropriate.

The composition can be made into an aerosol formulation to be administered via inhalation. Such aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Any suitable dosage level can be employed in the pharmaceutical compositions of the present invention. The dose administered to an animal, particularly a human, in the context of the present invention should be sufficient to effect a prophylactic or therapeutic response in the animal over a reasonable timeframe. The amount of active ingredient that can be combined with the carrier materials to produce a single dosage form will vary depending upon the host treated and the particular mode of administration. The size of the dose also will be determined by the existence, nature, and extent of any adverse side-effects that might accompany the administration of a particular composition. Suitable doses and dosage regimens for the prevention of drug resistance can be determined by comparisons to antiretroviral chemotherapeutic agents that are known to inhibit the proliferation of a retrovirus in an infected individual. The preferred dosage is the amount that results in the inhibition of the emergence of mutant drug-resistant retroviruses, particularly the emergence of multidrug-resistant retroviral HIV, without significant side effects. In proper doses and with suitable administration of certain compounds, a wide range of antiretroviral chemotherapeutic compositions are possible. A suitable dose includes a dose or dosage which would be insufficient to completely suppress the growth of a wild-type or predecessor virus, but would be sufficient to inhibit or effectively suppress the growth of a mutant.

In accordance with the present invention, the compound or composition can be administered in combination with other antiretroviral compounds such as, for example, ritonavir, amprenavir, saquinavir, indinavir, AZT, ddI, ddC, D4T, lamivudine, 3TC, and the like, as well as admixtures and combinations thereof, in a pharmaceutically acceptable carrier. The individual daily dosages for these combinations can range from about one-fifth of the minimally recommended clinical dosages to the maximum recommended levels for the entities when they are given singly.

The present invention also provides a method of preventing the emergence of multidrug-resistant retroviruses in an HIV-infected mammal, which method comprises administering to the mammal a multidrug resistance-inhibiting effective amount of a compound of the present invention, so as to inhibit the emergence of a multidrug-resistant retrovirus in the mammal. The dose administered to an animal, particularly a human in the context of the present invention, should be sufficient to effect a therapeutic response in the animal over a reasonable time frame. The dose will be determined by the strength of the particular composition employed and the condition of the animal, as well as the body weight of the animal to be treated. The size of the dose will also be determined by the existence, nature, and extent of any adverse side-effects that might accompany the administration of a particular compound. Other factors which effect the specific dosage include, for example, bioavailability, metabolic profile, and the pharmacodynamics associated with the particular compound to be administered in a particular patient. One skilled in the art will recognize that the specific dosage level for any particular patient will depend upon a variety of factors including, for example, the activity of the specific compound employed, the age, body weight, general health, sex, diet, time of administration, route of administration, rate of excretion, drug combination, CD4 count, the potency of the active compound with respect to the particular mutant retroviral strain to be inhibited, and the severity of the symptoms presented prior to or during the course of therapy. What constitutes a resistance-inhibiting effective amount can be determined, in part, by use of one or more of the assays described herein, particularly the fitness assay of the present invention.

One skilled in the art will appreciate that suitable methods of administering compounds and pharmaceutical compositions are available, and, although more than one route can be used to administer a particular composition, a particular route can provide a more immediate and/or more effective reaction than another route.

Numerous compounds have been identified that exhibit potent antiretroviral activity, in particular retroviral protease activity, against wild-type HIV. However, among the fifteen currently FDA-approved antiretroviral agents which are all known potent inhibitors of wild-type HIV, five of which are potent inhibitors of wild-type HIV protease, none of these compounds have the ability to prevent the emergence of drug-resistance mutations that are associated with high level cross resistance. Thus, these inhibitors do not have the ability to suppress the sufficiently fit mutant retroviruses that can (and almost certainly will) emerge under the selection pressure of these inhibitors.

Surprisingly, it has been discovered that compound 32 (shown in FIG. 3A), which is a potent wild-type HIV inhibitor, possesses remarkably potent and unprecedented broad-spectrum inhibitory activity against a panel of recombinant mutant HIV protease targets. These enzymes represent the key or primary resistance mutations, most of which occur in the active site region. Based on this finding, the compound was tested against a panel of drug resistant mutant patient isolates of HIV and was found to possess broad spectrum antiviral activity against a wide range of clinically isolated, multiply drug-resistant, human immunodeficiency viruses. Other compounds described herein showed similar activity. The mutant viruses were obtained from infected humans who had received several antiviral drugs. Although applicants do not wish to abound by any one particular theory, it is believed that the combination of the bicyclic ligand (vii) with isostere (vi) gives the antiretroviral compounds of the present invention the unique ability to bind to the active site of the mutant proteases of multiply drug-resistant human immunodeficiency viruses generally, which trait has heretofore not been reported with respect to any known chemotherapeutic and/or experimental HIV protease inhibitor. A wild-type preliminary screen was utilized to determine the antiretroviral activity of analogs against wild-type HIV. It is predicted that compounds of Formula (I), which have potent antiretroviral or protease-inhibitory activity against wild-type HIV, also will be potent inhibitors of drug-resistance, even multiple drug-resistance, in wild-type HIV, or even a mutant thereof.

Figure 4:
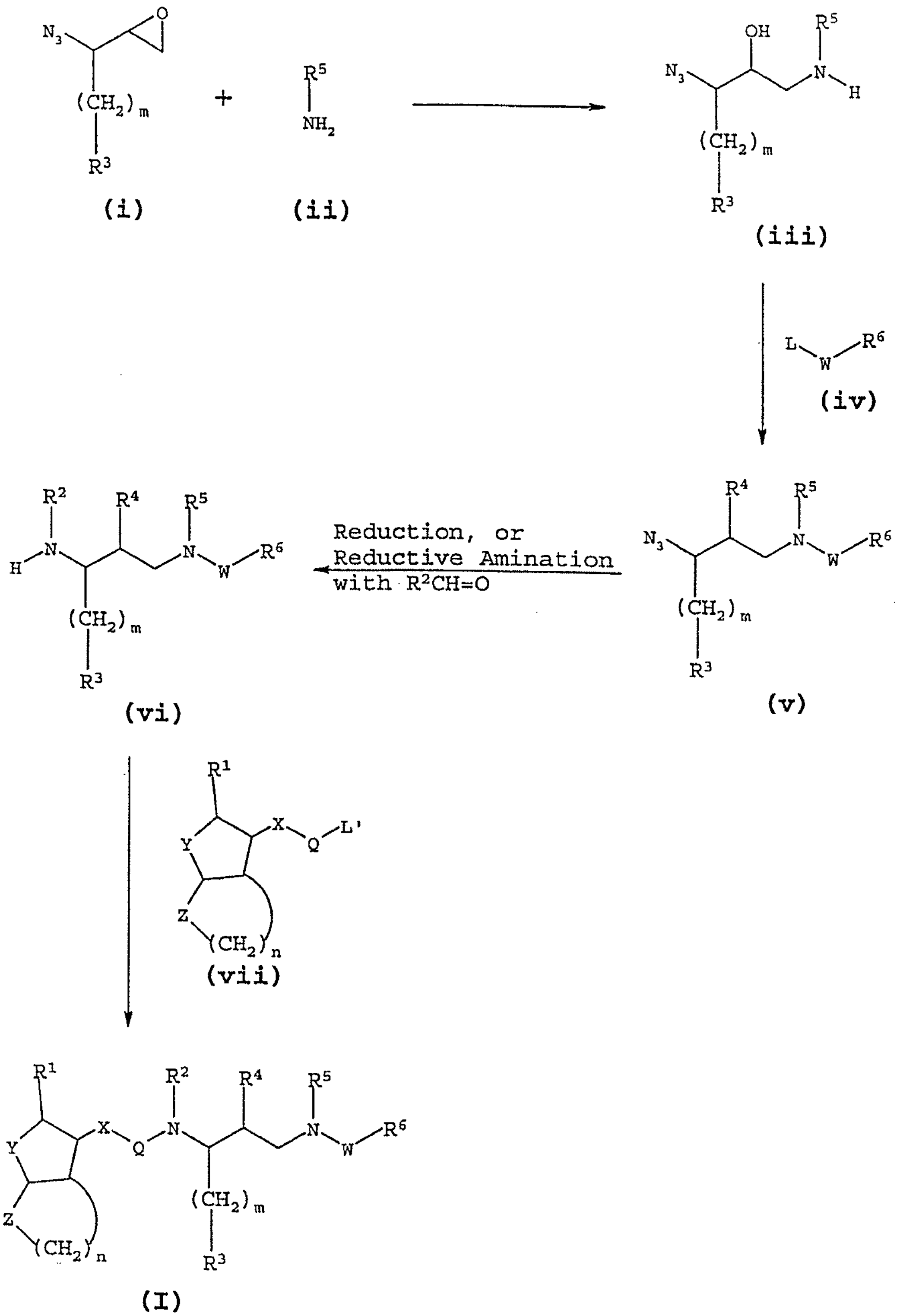
FIG. 4 illustrates generally the present method of synthesizing a compound of the present invention.

The resistance-inhibiting compounds of the present invention can be synthesized by any suitable method known in the art. The preferred synthesis method is generally illustrated in FIG. 4, which is an representation of the synthetic approach to preparing a preferred series of compounds, wherein a compound of Formula (I) is synthesized in several steps starting from azidoepoxide (i), wherein $R^1$-$R^{17}$, m, n, p, Q, W, X, y, and z are defined as above. Referring to FIG. 4, amine (ii) is nucleophilically added to azidoepoxide (i), providing aminoalcohol (iii). The amine functional group of aminoalcohol (iii) is then reacted with intermediate (iv), wherein L represents a leaving group (e.g., halogen, N-oxysuccinimide), which can be displaced by the amine of aminoalcohol (iii), to provide azide (v). Reduction of azide (v), or, when $R^5$ is not hydrogen, reductive amination with aldehyde $R^5CH{=}O$, provides intermediate (vi), which is subsequently coupled with activated bicyclic ligand (vii), to provide compounds of Formula I. Of course, it will be appreciated by a person of ordinary skill in the art that there are combinations of substituents, functional groups, R-groups, and the like, which are reactive under particular reaction conditions, and require the utilization of an appropriate protecting group or groups, which are known in the art, to ensure that the desired synthetic transformation will take place without the occurrence of undesired side reactions. For example, possible substituents at $R^5$ (e.g., $NH_2$)

can be competitive nucleophiles requiring the attachment of an appropriate protecting group thereon (e.g., benzyloxycarbonyl, tert-butoxycarbonyl) in order obtain proper selectivity in the ring opening of epoxide (i) with amine (ii).

FIGS. 1-3B illustrate the synthesis of a preferred series of compounds for use in the method of preventing the emergence of resistance in accordance with the present invention. FIG. 1, which is a synthetic scheme for the synthesis of a particular sulfonamide, illustrates the synthesis of a preferred isosteric core, particularly, the sulfonamide isosteric core represented by aminosulfonamide 15. With reference to FIG. 1, aminosulfonamide core 15 can be synthesized by initially providing azidoepoxide 11 and subjecting it to nucleophilic addition with amine 12 to give aminoalcohol 13, which is subsequently converted to sulfonamide 14 by reaction with 4-methoxybenzenesulfonyl chloride. The azide group of 14 is then reduced to provide aminosulfonamide 15, which can be used as a core for synthesizing numerous multidrug-resistant retroviral protease inhibitors of the present invention.

Figure 2:
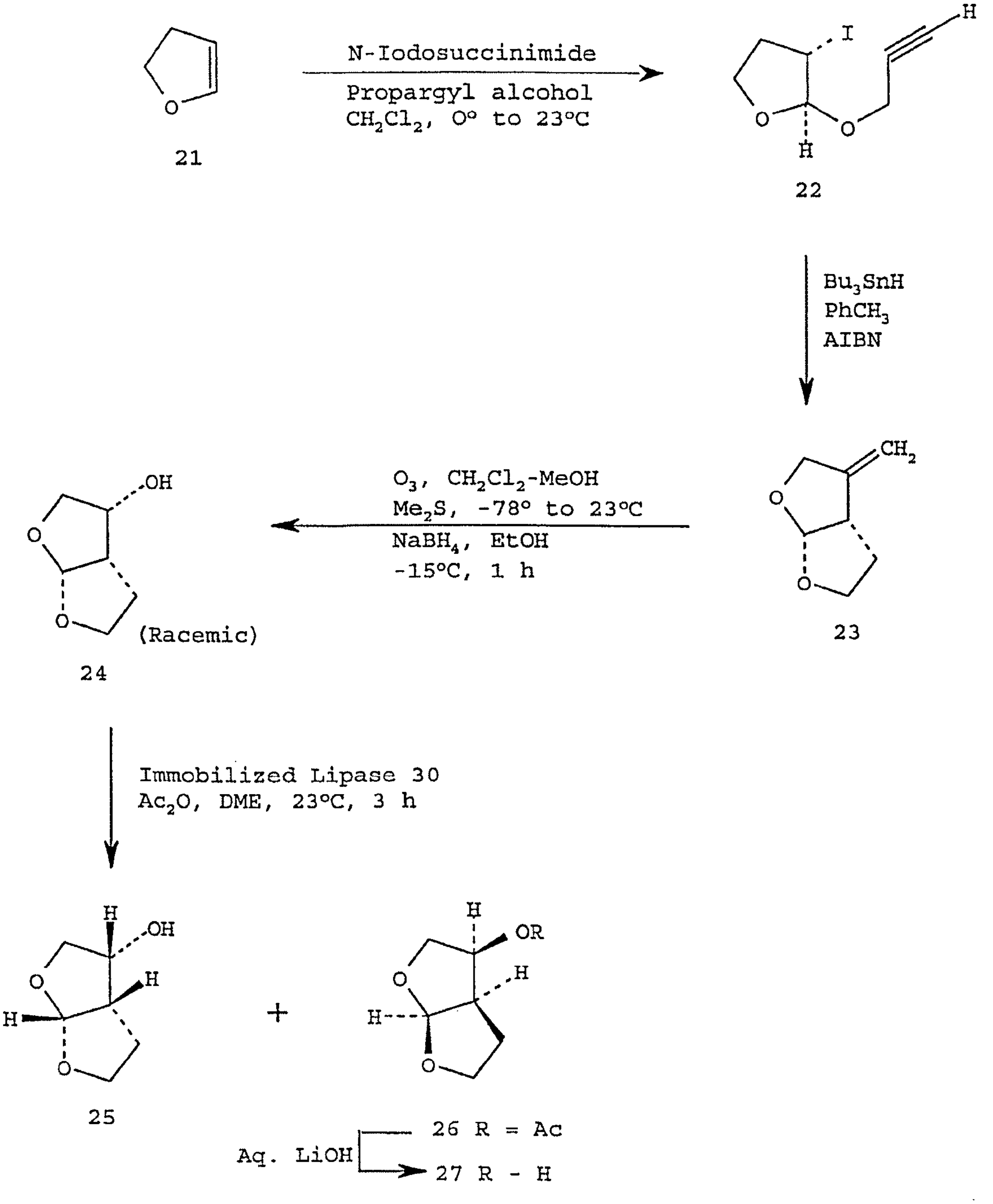
FIG. 2 illustrates the synthesis of a bis-tetrahydrofuran ligand and the optical resolution thereof.

FIG. 2, which is a reaction scheme detailing the preparation of bicyclic alcohols, illustrates the synthesis of a preferred series of bicyclic ligands, particularly bis-tetrahydrofurans 25 and 26. With reference to FIG. 2, dihydrofuran 21 is treated with N-iodosuccinimide in the presence of propargyl alcohol to give iodoether 22, which is cyclized to methylene-substituted bis-tetrahydrofuran 23. Ozonolysis of the exo-methylene residue of 23, followed by reduction, provides bicyclic racemic alcohol 24, which is resolved to give, separately, bicyclic alcohol 25 and its enantiomeric acetate ester 26, which ester group of 26 is subsequently hydrolyzed to afford enantiomer 27.

Figure 3A:
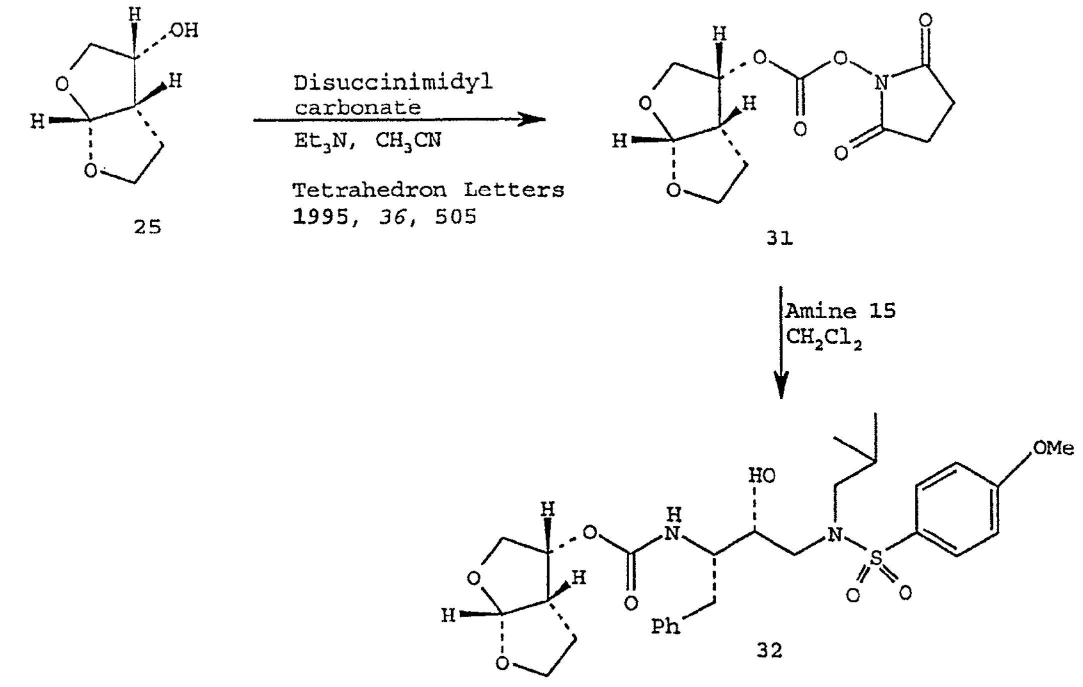
FIG. 3A illustrates the synthesis of a compound of the present invention via coupling of a bis-tetrahydrofuran ligand to a sulfonamide isostere of the present invention.
Figure 3B:
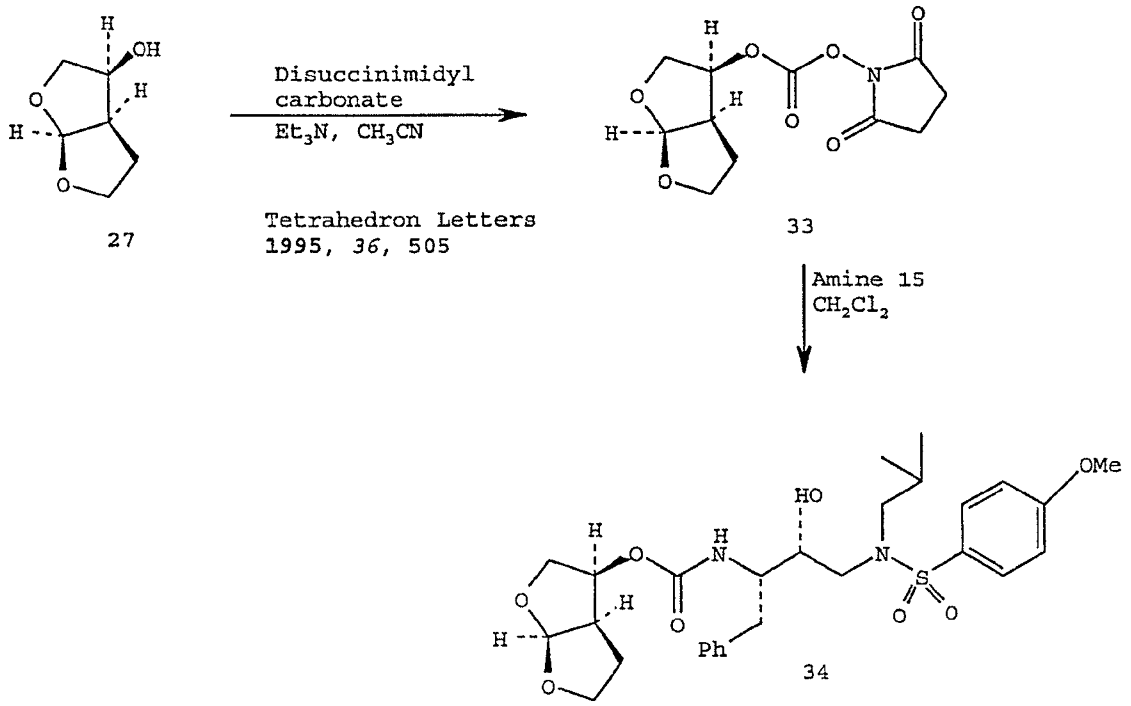
FIG. 3B illustrates the synthesis of a compound of the present invention via coupling of a bis-tetrahydrofuran ligand to a sulfonamide isostere of the present invention.

FIGS. 3A and 3B, which are reaction schemes describing the preparation of two protease inhibitors, illustrate the preparation of two preferred multidrug-resistant HIV protease inhibitors of the present invention. With reference to FIG. 3A, compound 32 was synthesized by coupling succinimidocarbonate 31 with aminosulfonamide 15. Succinimidocarbonate 31 was prepared by reacting optically pure bicyclic alcohol 25 with disuccinimidyl carbonate in the presence of triethylamine. Inhibitor 34, which possesses the enantiomeric bis-tetrahydrofuranyl ligand (relative to inhibitor 32), was prepared in the same fashion, except that the enantiomeric bicyclic alcohol 27 was used instead of alcohol 25, as illustrated in FIG. 3B.

The following examples further illustrate the present invention but, of course, should not be construed as in any way limiting its scope.

EXAMPLE 1

This example describes the synthesis of exemplary epoxide 11 (FIG. 1), which is used as an intermediate in the synthesis of a particular series of compounds within the scope of the present invention.

Anhydrous CuCN (4.86 g, 54 mmol) was added to a solution of butadiene monooxide (38 g, 540 mmol) in anhydrous tetrahydrofuran (1.2 L) and the resulting mixture was stirred at −78° C. Commercial phenyl magnesium bromide solution (Aldrich) in ether (65 mmol) was added dropwise over a period of 10 min. The resulting reaction mixture was then allowed to warm to 0° C. and it was continued to stir until the reaction mixture was homogeneous. After this period, the reaction mixture was cooled to −78° C. and 0.58 mole of phenylmagnesium bromide solution in ether was added dropwise for 30 min. The reaction mixture was allowed to warm to 23° C. for 1 h. The reaction was quenched by slow addition of saturated aqueous $NH_4Cl$ (120 mL) followed by $NH_2OH$ (70 mL), saturated $NH_4Cl$ (500 ML) and then $H_2O$ (300 mL). The aqueous layer was thoroughly extracted with ethyl acetate (2×300 mL). The combined organic layers were dried over anhydrous $Na_2SO_4$, filtered, and concentrated under reduced pressure. The residue was distilled under vacuum (0.12 torr) at 95° C. to give trans-4-phenyl-2-butene-1-ol (75.6 g).

To a suspension of powdered 4 Å molecular sieves (6.6 g) in anhydrous methylene chloride (750 mL), titanium tetraisopropoxide (Aldrich, 3.2 mL) and then diethyl D-tartrate (2.3 mL) were added. The resulting mixture was cooled to −22° C. and tert-butylhydroperoxide solution in isooctane (Aldrich, 430 mmol) was added over a period of 10 min. The mixture was stirred an additional 30 min and then a solution of trans-4-phenyl-2-butene-1-ol (32.6 g, 213 mmol), in anhydrous methylene chloride (120 mL), was added dropwise over a period of 40 min at −22° C. The reaction mixture was then aged in a freezer at −22° C. for 24 h. After this period, water (100 mL) was added to the reaction mixture at −22° C. and the mixture was allowed to warm to 0° C. After stirring at 0° C. for 45 min, 20% NaOH in brine (20 mL) was added. The resulting mixture was then allowed to warm to 23° C. and was stirred at that temperature for 1 h. After this period, the layers were separated and the aqueous layer was extracted with methylene chloride (2×200 mL). The combined organic layers were dried over anhydrous $Na_2SO_4$ and concentrated under reduced pressure. The residue was diluted with toluene (800 mL) and then evaporated under reduced pressure. The residue was chromatographed over silica gel (35% ethyl acetate in hexane as eluent) to provide (2R,3R)-epoxy-4-phenylbutan-1-ol (21.8 g).

To a solution of titanium ispropoxide (12 mL) in anhydrous benzene (250 mL) was added azidotrimethylsilane (11 mL) and the resulting mixture was refluxed for 6 h. A solution of (2R,3R)-epoxy-4-phenylbutan-1-ol (5.32 g) in anhydrous benzene (25 mL) was added to the above refluxing mixture. The resulting mixture was refluxed for addition 25 min. After this period, the reaction mixture was cooled to 23° C. and the reaction was quenched with aqueous 5% $H_2SO_4$ (400 mL). The resulting mixture was stirred for 1 h and the layers were separated and the aqueous layer was extracted with ethyl acetate (2×300 mL). The combined organic layers were washed with saturated $NaHCO_3$ (200 mL), dried over $Na_2SO_4$ and concentrated under reduced pressure to afford the (2S,3S)-2-hydroxy-3-azido-4-phenylbutan-12-ol (5.1 g) as a white solid (mp 81-82° C.).

To a stirred solution of the azidodiol (5.1 g) in chloroform (100 mL) at 23° C., 2-acetoxyisobutyryl chloride (Aldrich, 5 mL) was added. The resulting reaction mixture was stirred at 23° C. for 8 h. The reaction was quenched by addition of saturated sodium bicarbonate (100 mL) and the resulting mixture was stirred 30 min. The layers were separated and the aqueous layer was extracted with chloroform (2×200 mL). The combined organic layer was extracted with chloroform (2×200 mL). The combined organic layers were dried over $Na_2SO_4$ and evaporated under reduced pressure. The resulting residue was dissolved in anhydrous THF (50 mL) and solid NaOMe (2.1 g) was added. The mixture was stirred for 4 h at 23° C. and after this period, the reaction was quenched with saturated $NH_4Cl$ (50 mL). The resulting mixture was extracted with ethyl acetate (2×200 ML). The combined organic layers were dried over anhydrous $Na_2SO_4$ and concentrated under reduced pressure to give a residue, which was chromatographed over silica gel (10% ethyl acetate in hexanes) to afford the 3(S)-azido-(1,2R)-epoxy-4-phenylbutane 11 (3.3 g) as an oil: $^1H$ NMR (300 MHz):

$CDCl_3$; δ 7.4-7.2 (m, 5H,), 3.6 (m, 1H), 3.1 (m, 1H), 2.95 (dd, 1H, J=4.6, 13.9 Hz), 2.8 (m, 3H).

EXAMPLE 2

This example illustrates the synthesis of azidoalcohol 13 (FIG. 1), which can be used as an intermediate in the synthesis of a preferred series of the compounds of the present invention.

To a stirred solution of above azidoepoxide 11 (700 mg, 3.7 mmol) in ispropanol (70 mL) was added isobutyl amine (Aldrich, 0.74 mL 7.4 mmol) and the resulting mixture was heated at 80° C. for 12 h. After this period, the reaction mixture was concentrated under reduced pressure and the residue was chromatographed over silica gel to provide azidoalcohol 13 (800 mg) as an oil.

EXAMPLE 3

This example illustrates the synthesis of azidosulfonamide 14, the structure of which is shown in FIG. 1.

To a stirred solution of 13 (600 mg, 2.28 mmol) in $CH_2Cl_2$ (20 mL) was added 4-methoxybenzenesulfonyl chloride (Aldrich, 530 mg, 2.52 mmol) and saturated aqueous $NaHCO_3$ (6 mL). The resulting heterogeneous mixture was stirred at 23° C. for 12 h. The reaction was diluted with $CH_2Cl_2$ and the layers were separated. The organic layer was washed with brine, dried over anhydrous magnesium sulfate and concentrated to dryness. The residue was chromatographed over silica gel (25% ethyl acetate/hexane) to provide 900 mg of azidosulfonamide 14.

EXAMPLE 4

This example illustrates the preparation of aminosulfonamide 15 via reduction of azidosulfonamide 14, as shown in FIG. 1.

A solution of 14 (1.53 g) in THF (45 mL), NeOH (10 mL) and acetic acid (0.5 mL), was shaken with 10% palladium on carbon catalyst (200 mg) at 50 psi hydrogen pressure for 2 h. Removal of the catalyst by filtration over celite and concentration under reduced pressure gave a crude residue, which was diluted with $CH_2Cl_2$ (100 mL), and was washed successively with saturated aqueous $NaHCO_3$ and brine. The organic layer was dried over $MgSO_4$ and concentrated to give the corresponding aminosulfonamide 15 (1.2 g).

EXAMPLE 5

This example demonstrates the synthesis of trans-2-(propargyloxy)-3-iodotetrahydrofuran 22 (FIG. 2).

To a stirred, ice-cold suspension of 15 g (66.6 mmol) of N-iodosuccinimide in 150 mL of $CH_2Cl_2$ was added a mixture of dihydrofuran 21 (66.6 mmol, 4.67 g, 5.1 mL) and propargyl alcohol (100 mmol, 5.0 g, 5.2 mL) of in 50 mL of $CH_2Cl_2$ over 20 min. After warming to 24° C. with stirring over 2 h, 200 mL of water were added and the stirring continued for 1 h. The layers were separated and the aqueous layer was extracted with 2×100 mL of $CH_2Cl_2$. The combined organic extracts were washed with brine solution containing small amount of $Na_2S_2O_3$ (70 mg), dried over anhydrous $Na_2SO_4$, filtered, and concentrated. Chromatography over silica gel using 30% ethyl acetate in hexane afforded (15.4 g, 92%) the title iodoether 22 as an oil.

EXAMPLE 6

This example illustrates the synthesis of (±)-(3aR, 6aS) and (3aS,6aR)-3-methylene-4H-hexahydrofuro-[2,3-b]furan 23, as shown in FIG. 2.

To a refluxing solution of (20.7 mL, 77 mmol) tributyltin hydride containing AIBN (100 mg) in toluene (200 mL) was added dropwise a solution of 15.4 g (61 mmol) of iodotetrahydrofuran 22 in toluene (50 mL) over a period of 1 h. The resulting mixture was stirred at reflux for an additional 4 h (monitored by TLC). The mixture was then cooled to 23° C. and concentrated under reduced pressure. The residue was partitioned between petroleum ether and acetonitrile (200 mL of each) and the acetonitrile (lower) layer was concentrated. The residue was purified by chromatography on silica gel, using 10 ethyl acetate in hexane as the eluent to provide the title product 23 (5.84 g, 76%) as an oil.

EXAMPLE 7

This example demonstrates the synthesis of (±)-(3SR, 3aRS, 6aS) and (3R,3aS,6aR)-3-hydroxy-4H-hexahydrofuro[2,3-b]furan 24, as shown in FIG. 2.

A stream of ozone was dispersed into a solution of 15 (5.84 g, 46.4 mmol) at −78° C. in 150 mL of methanol and 150 mL of $CH_2Cl_2$ for 30 min. The resulting blue solution was purged with nitrogen until colorless, then quenched with 20 mL of dimethyl sulfide and the resulting mixture was allowed to warm to 23° C. The mixture was concentrated under reduced pressure to afford the crude ketone. The resulting crude ketone was dissolved in ethanol (50 mL) and the solution was cooled to 0° C. and sodium borohydride (2.1 g, 55.6 mmol) was added. The reaction mixture was stirred for an additional 2 h at 0° C. and then quenched with 10% aqueous citric acid (10 mL). The resulting mixture was concentrated under reduced pressure and the reside was partitioned between ethyl acetate and brine. The layers were separated and the aqueous layer was extracted with ethyl acetate (2×100 mL). The combined organic layers were dried over anhydrous-$Na_2SO_4$ and concentrated carefully under reduced pressure. The resulting residue was chromatographed over silica gel using 30% ethyl acetate in hexane as the eluent to furnish (4.52 g, 75%) the title racemic alcohol 24 as an oil.

EXAMPLE 8

This example illustrates the preparation of immobilized Amano Lipase 30, which was used to resolve racemic aminoalcohol 24 (FIG. 2).

Commercially available 4 g of Celite® 521 (Aldrich) was loaded on a buchner funnel and washed successively with 50 mL of deionized water and 50 mL of 0.05; N phosphate buffer (pH=7.0; Fisher Scientific). The washed celite was then added to a suspension of 1 g of Amano lipase 30 in 20 mL of 0.05; N phosphate buffer. The resulting slurry was spread on a glass dish and allowed to dry in the air at 23° C. for 48 h (weight 5.4 g; water content about 2% by Fisher method).

EXAMPLE 9

This example demonstrates the synthesis of (3R,3aS, 6aR)3-hydroxyhexahydrofuro[2,3-b]furan 25 by immobilized lipase catalyzed acylation, as illustrated in FIG. 2.

To a stirred solution of reacemic alcohol 24 (2 g, 15.4 mmol) and acetic anhydride (4 g, 42.4 mmol) in 100 mL of DME was added 2.7 g (about 25% by weight of lipae PS30) of immobilized Amano lipase and the resulting suspension was stirred at 23° C. The reaction was monitored by TLC and $^1H$ NMR analysis until 50% conversion was reached. The reaction mixture was filtered and the filter cake was washed repeatedly with ethyl acetate. The combined filtrate was carefully concentrated in a rotary evaporator, keeping the bath temperature below 15° C. The residue was chromatographed over silica gel to provide 843 mg (42%) of 25 (95% ee; $a_D^{23°}$−11.9°, MeOH); $^1$H-NMR ($CDCl_3$) d 1.85 (m, 2H), 2.3 (m, 1H), 2.9 (m, 1H), 3.65 (dd, J=7.0, 9.1, 1H), 3.85-4.0 (m, 3H), 4.45 (dd, J=6.8, 14.6, 1H), 5.7 (d, J=5.1, 1H); also, 1.21 g of 26 after washing with 5% aqueous sodium carbonate (45%, $a_D^{23°}$+31.8°, MeOH); $^1$H-NMR ($CDCl_3$)d 1.85-2.1 (m, 2H), 2.1 (s, 3H), 3.1 (m, 1H), 3.75 (dd, J=6.6, 9.2, 1H), 3.8-4.1 (m, 3H), 5.2 (dd, J=6.4, 14.5, 1H), 5.7 (d, J=5.2, 1H). Acetate 26 was dissolved in THF (5 mL) and 1 M aqueous LiOH solution (20 mL) was added to it. The resulting mixture was stirred at 23° C. for 3 h and the reaction was extracted with chloroform (3x25 mL). The combined organic layers were dried over anhydrous $Na_2SO_4$ and evaporated under reduced pressure. The residue was chromatographed over silica gel to provide 733 mg of 27 (97% ee; $\alpha_D^{23°}$-12.5°, MeOH).

EXAMPLE 10

This example demonstrates the synthesis of activated carbonates 31 and 33, as illustrated in FIGS. 3A and 3B.

To a stirred solution of [3R,3aS,6aS]-3-hydroxyhexahydrofuro[2,3-b]furan 25 (65 mg, 0.5 mmol) in dry $CH_3CN$ (5 mL) at 23° C. were added disuccinimidyl carbonate (192 mg, 0.75 mmol) and triethylamine (0.25 mL). The resulting mixture was stirred at 23° C. for 12 h. The reaction was quenched with saturated aqueous $NaHCO_3$ (10 mL) and the mixture was concentrated under reduced pressure. The residue was extracted with $CH_2Cl_2$ (2x25 mL) and the combined organic layers were washed with brine (10 mL) and dried over anhydrous $Na_2SO_4$. Evaporation of the solvent under reduced pressure gave a residue, which was chromatographed over silica gel (50% ethyl acetate/hexane) to furnish (3R,3aS,6aR)3-hydroxyhexahydrofuro[2,3-b]furanyl-succinimidyl carbonate 31 (70 mg) as a brown oil. Carbonate 33 (65 mg) was prepared from 60 mg of alcohol 27 by following a similar procedure.

EXAMPLE 11

This example illustrates the preparation of multidrug-resistant HIV inhibitor 32, as illustrated in FIG. 3A.

To a stirred solution of amine 15 (82 mg, 0.2 mmol) in dry $CH_2Cl_2$ (5 mL) was added succinimidyl carbonate 31 (55 mg, 0.18 mmol). The resulting solution was stirred at 23° C. for 12 h. After this period, the reaction was quenched with saturated aqueous $NaHCO_3$ (10 mL) and diluted with $CH_2Cl_2$ (25 mL). The layers were separated and the organic layer was washed with brine (15 mL) and dried over anhydrous $Na_2SO_4$. Evaporation of the solvent under reduced pressure afforded a residue, which was purified by silica gel chromatography (75% ethyl acetate/hexane) to furnish compound 32 (85 mg) as a white solid (m.p 55-58° C.). $^1$H-NMR ($CDCl_3$, 400 MHz); δ 7.71 (d, 2H, J=8.8 Hz), 7.29-7.20 (m, 5H), 6.99 (d, 2H, J=7.0 Hz), 5.65 (d, 1H, J=5.19), 5.01 (m, 2H), 3.95-3.82 (m, 7H), 3.69 (m, 2H), 3.0-2.7 (m, 6H), 1.85 (m, 1H), 1.64-1.45 (m, 3H), 0.90 (two d, 6H, J=6.5 Hz, 6.6 Hz).

EXAMPLE 12

This example illustrates the preparation of multidrug-resistant HIV inhibitor 33, as illustrated in FIG. 3B.

Carbonate 33 (55 mg) was reacted with amine 15 (82 mg, 0.2 mmol) according to the procedure mentioned above to provide compound 34 (81 mg). $^1$H-NMR ($CDCl_3$, 300 MHz); δ 7.69 (d, 2H, J=8.8 Hz), 7.28-7.21 (m, 5H), 6.87 (d, 2H, J=5.84 Hz), 5.67 (d, 1H, J=5.46 Hz), 5.0 (m, 2H), 3.86-3.81 (m, 7H), 3.58 (dd, 2H, J=6.6 Hz, 3.6 Hz, 3.17-2.73 (m, 6H), 2.17-1.83 (m, 4H), 0.90 (two d, 6H, J=6.5 Hz, 6.6 Hz).

EXAMPLE 13

This example describes the protocol for the sensitive continuous fluorogenic assay for HIV protease of the present invention and its application. Using this assay, the inhibitory activity of compound 32 (FIG. 3A) was tested against the proteases of wild-type HIV-1 (WT) and various mutant enzymes: D30N, V32I, I84V, V32I/I84V, M46F/V82A, G48V/L90M, V82F/I84V, V82T/I84V, V32I/K45I/F53L/A71V/I84V/L89M, V32I/L33F/K45I/F53L/A71V/I84V, and 20R/36I/54V/71V/82T, which protease enzymes are available from Dr. John W. Erickson, Structural Biochemistry Program, SAIC Frederick, P.O. Box B, Frederick, Md. 21702-1201, upon written request. The inhibition constant for wild-type HIV-1, $K_{imnt}/K_{iwt}$ ratio, and vitality were measured. (See Gulnik et al., *Biochemistry,* 34, 9282-9287 (1995). Protease activity was measured using the fluorgenic substrate Lys-Ala-Arg-Val-Tyr-Phe($NO_2$)-Glu-Ala-Nle-$NH_2$ (Bachem Bioscience, Inc.). (See Peranteau et al., D.H. (1995) *Anal. Biochem.*).

Typically, 490 μl of 0.125 M ACES-NaOH buffer, pH 6.2, containing 1.25 M $(NH_4)_2SO_4$, 6.25 mM DTT and 0.1% PEG-8000 was mixed with 5 μl of titrated protease (final concentration 1-5 nM) and incubated 3 min at 37° C. The reaction was initiated by the addition of 5 μl of substrate stock solution in water. Increase in fluorescence intensity at the emission maximum of 306 nm (excitation wavelength was 277 nm) was monitored as a function of time using Aminco Bowman-2 luminescence spectrometer (SLM Instruments, Inc.). The initial rate of hydrolysis was calculated by second degree polynomial fit using SLM AB2 2.0 operating software. Kinetic parameters were determined by nonlinear regression-fitting of initial rate versus substrate concentration data to the Michaelis-Menten equation using program Enzfiter version 1.05.

For inhibition studies, inhibitors were prepared as stock solutions at different concentrations in dimethylsulfoxide. In a typical experiment 485 μl of 0.125 M ACES-NaOH buffer, pH 6.2, containing 1.25 M $(NH_4)_2SO_4$, 6.25 mM DTT AND 0.1% PEG-8000, was mixed with 5 μl of inhibitor stock solution and 5 μl of titrated protease (final concentration of 1-5 nM) and preincubated 3 min at 37° C. The reaction was initiated by the addition of 5 μl of substrate stock solution in water. For data analysis, the mathematical model for tight-binding inhibitors was used. (See Williams and Morrison (1979), In: Methods of Enzymol. 63, (ed. D. L. Purich), 437-467, Academic Press, NY, London). The data were fitted by nonlinear regression analysis to the equation:

$$V=V_0/2E_t(\{[K_i(1+S/K_m)+I_t-E_t]^2+4K_i(1+S/K_m)E_t\}^{1/2}-[K_i((1+S/K_m)+I_t-E_t])$$

with the program Enzfiter (version 1.05), where V and $V_0$ are initial velocities with and without inhibitor, respectively, $K_m$ is a Michaelis-Menten constant, and S, $E_t$ and $I_t$ are the concentrations of substrate, active enzyme, and inhibitor, respectively. Biochemical fitness for each mutant was determined by comparing the biochemical vitality of each mutant (vitality$_{mut}$) with the biochemical vitality of the wild-type reference (vitality$_{wt}$), according to the formula $$(\text{vitality}_{mut})/(\text{vitality}_{wt})$$

wherein vitality is $(K_i)(k_{cat}/K_M)$. The results are shown below in Table 1.

TABLE 1

| Enzyme | Compound 32 $K_i$ (pM) | $K_{I\text{-}mut}/K_{I\text{-}wt}$ | Biochemical Fitness |
|---|---|---|---|
| WT | 14 | 1 | 1 |
| D30N | <5 | 0.33 | 0.3 |
| V32I | 8 | 0.57 | 0.5 |
| I84V | 40 | 2.85 | 1 |
| V32I/I84V | 70 | 5 | 0.7 |
| M46F/V82A | <5 | 0.33 | 0.1 |
| G48V/L90M | <5 | 0.33 | 0.1 |
| V82F/I84V | 7 | 0.5 | 0.1 |
| V82T/I84V | 22 | 1.57 | 0.1 |
| V32I/K45I/F53L/A71V/I84V/L89M | 31 | 2.2 | 0.1 |
| V32I/L33F/K45I/F53L/A71V/I84V | 46 | 3.3 | 0.1 |
| 20R/36I/54V/71V/82T | 31 | 2.2 | 0.1 |

The above results demonstrate that compound 32 is a potent inhibitor of multiple HIV protease mutants that contain the primary or key drug resistance mutations. These data predict that compound 32 will have potent and broad-spectrum multidrug-resistant antiretroviral activity. Moreover, the biochemical fitness of each mutant relative to wild type is equal to or less than one in the presence of compound 32. Based on this fitness profile, it is believed that drug resistant viruses containing the characteristic mutations assayed herein will not emerge from the wild-type in the presence of compound 32.

EXAMPLE 14

This example illustrates the potent and broad-spectrum multidrug-resistant antiretroviral activity of an exemplary compound of the present invention.

Compound 32, shown in FIG. 3A, was tested side-by-side with four other known HIV-1 protease inhibitors against various wild-type HIV-1 strains (HIV-$1_{ERS104pre}$, HIV-$1_{LAI}$, and HIV-$1_{BAL}$), and mutant multidrug-resistant HIV-1 strains clinically isolated from eight different patients who had received numerous antiviral drugs, either singly or in combination. The patients from which the mutant strains were isolated had a history of anti-HIV therapy with a variety of different drugs such as, for example, ritonavir, saquinavir, indinavir, amprenavir, AZT, ddI, ddC, d4T, 3TC, ABV (abacavir), DLV (delaviridine), and PFA (foscarnet). The patient profiles are shown below in Table 2.

TABLE 2

| Patient/ Isolate Code | $CD4^+$ (/mm$^3$) | HIV-1 RNA level (copies/mL) | Months on Antiviral Therapy | Prior and Present Anti-HIV Therapy |
|---|---|---|---|---|
| 1 | 361 | 246,700 | 64 | AZT, ddI, ddC, d4T, 3TC, ABV, IDV, RTV, SQV, AMV, DLV |
| 2 | 3 | 553,700 | 46 | AZT, ddI, ddC, d4T, 3TC, ABV, IDV, SQV, AMV |
| 3 | 108 | 42,610 | 39 | AZT, ddI, ddC, d4T, 3TC, ABV, IDV, SQV, AMV |
| 4 | 560 | 60,000 | 81 | AZT, ddI, ddC, U90, d4T, 3TC, ABV, IDV, SQV, AMV |
| 5 | — | — | 32 | AZT, ddI, ddC, d4T, 3TC, ABV, IDV, SQV, AMV |
| 6 | — | — | 34 | AZT, ddI, ddC, d4T, 3TC, ABV, IDV, SQV, AMV |
| 7 | — | — | 83 | AZT, ddI, ddC, d4T, 3TC, ABV, IDV, SQV, RTV, AMV |
| 8 | — | — | 69 | AZT, ddI, ddC, d4T, 3TC, PFA, ABV, IDV, SQV, AMV |

The four known chemotherapeutic HIV protease inhibitors used for comparative purposes in this example have been utilized in actual human HIV chemotherapy, and are: Ritonavir ("RTV," Abbott Laboratories); Indinavir ("IDV," Merck Research Laboratories); Amprenavir (AMV, See Ghosh et al., *Bioorg. Med. Chem. Lett.*, 8, 687-690 (1998)); and Saquinavir ("SAQ", Roche Research Centre). The $IC_{50}$ values (μM) for all five compounds were determined with respect to wild-type and multidrug-resistant HIV-1.

To determine protease inhibitory activity against multidrug resistant HIV, the $IC_{50}$'s were measured against a panel of clinically isolated mutant HIV isolates. The $IC_{50}$'s were determined by utilizing the PHA-PBMC exposed to HIV-1 (50 $TCID_{50}$ dose/1×10$^6$ PBMC) as target cells and using the inhibition of p24 Gag protein production as an endpoint.

The $IC_{50}$'s were determined by utilizing the PHA-PBMC assay in which target cells are exposed to HIV-1 (50 $TCID_{50}$ dose/1×10$^6$ PBMC) and inhibition of p24 Gag protein production is used as an endpoint. All drug sensitivities were performed in triplicate. In order to determine whether the HIV isolates were syncitium inducing (SI) or non-syncitium inducing (NSI), an aliquot of viral stock supernatant, containing 100 $TCID_{50}$, was cultured with 1×10$^5$ MT-2 cells in a 12-well plate. Cultures were maintained for four weeks and were examined for syncytium formation twice a week. The results are shown below in Table 3.

TABLE 3

| | | $IC_{50}$ (μM) | | | | |
|---|---|---|---|---|---|---|
| Phenotype | Patient/ Isolate code (See Table 2) | RTV | IDV | AMV | SAQ | Compound 32 |
| SI | HIV-$1_{ERS104pre}$ | 0.055 | 0.013 | 0.021 | 0.01 | <0.001 |
| SI | HIV-$1_{LAI}$ | 0.0047 | 0.019 | 0.019 | 0.0054 | 0.0004 |
| NSI | HIV-$1_{BAL}$ | 0.018 | 0.0056 | 0.014 | 0.0037 | 0.0004 |
| | 1 | >1 | >1 | 0.29 | 0.29 | 0.002 |
| | 2 | >1 | 0.24 | 0.24 | 0.035 | <0.001 |
| | 3 | >1 | 0.46 | 0.33 | 0.036 | <0.001 |
| | 4 | >1 | 0.24 | 0.4 | 0.033 | 0.001 |
| NS1 | 5 | >1 | 0.8 | 0.28 | 0.24 | 0.002 |
| | 6 | >1 | 0.37 | 0.11 | 0.19 | <0.001 |
| | 7 | >1 | >1 | 0.42 | 0.12 | 0.004 |
| | 8 | >1 | >1 | 0.22 | 0.009 | 0.001 |

The above $IC_{50}$'s clearly demonstrate the broad-spectrum and extraordinarily potent activity of compound 32 against wild-type HIV-1 and the eight different multidrug-resistant clinical isolates tested as was predicted from the biochemical fitness profiles in Example 13. For example, compound 32 exhibits nanomolar and sub-nanomolar potency against all the multidrug-resistant strains tested, whereas Ritonavir, a reasonably potent wild-type inhibitor, is virtually inactive toward the resistant viruses. Moreover, compound 32 is about 9 to about 150 times more potent against the multi-drug-resistant viruses than Saquinavir, one of the most potent known compounds against known multidrug-resistant strains of HIV-1. Patients with viral plasma loads greater than 10,000 RNA copies/$mm^3$ are at risk for developing fatal AIDS complications. There are no effective therapeutic options currently available for these patients infected with these multidrug resistant viruses. Compound 32 and analogs thereof are predicted to be potent in preventing the selection of these viral strains in vivo.

EXAMPLE 15

This example demonstrates the wild-type antiretroviral activity of the compounds of the present invention.

It is predicted that the activity of the present inventive compounds against wild-type HIV protease correlates with of antiretroviral activity against multidrug-resistant HIV. Numerous compounds of the present invention were tested against wild-type HIV (See, Ghosh et al., *J. Bioorg. Med. Chem. Lett.,* 8, 6870690 (1998)). Exemplary compounds, which demonstrate potent wild-type HIV protease activity, are shown below in Table 4.

TABLE 4

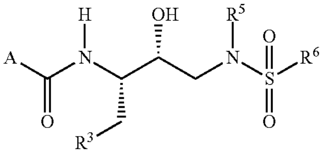

| A | $R^3$ | $R^5$ | $R^6$ | Ki (nM) | $ID_{50}$ (nM) | Comments |
|---|---|---|---|---|---|---|
| 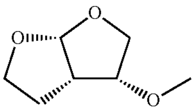 | Ph | 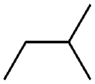 | 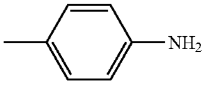 | 2.1 | 4.5 | Compound 32 (FIG. 3A) Compound 34 (FIG. 3B) |
| 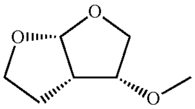 | Ph | 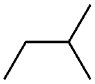 | 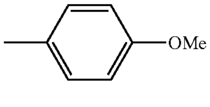 | 1.1 | 1.4 | |
| 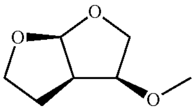 | Ph | 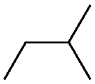 | 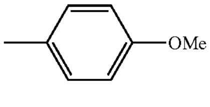 | | | |
| 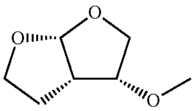 | Ph | 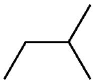 | 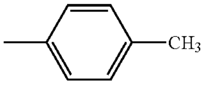 | 1.2 | 3.5 | |
| 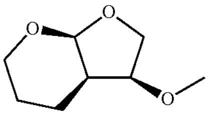 | Ph | 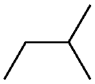 | 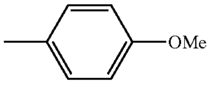 | 2.2 | 4.5 | |
| 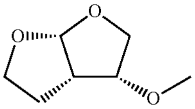 | Ph | 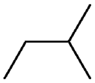 | 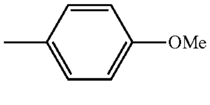 | | | |
| 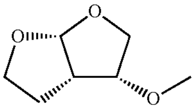 | 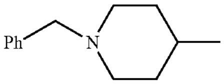 | 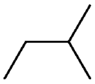 | 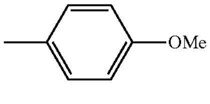 | | | |
| 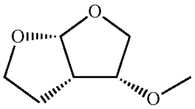 | Ph | 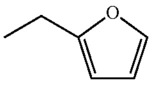 | 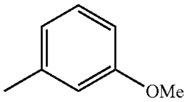 | | | |

It is believed that the above compounds in Table 4 will prevent the emergence of resistance in an HIV-infected human.

EXAMPLE 16

This example demonstrates the oral absorption of compound 32 in an in vivo experimental model.

Compound 32 was orally administered to a rat at a dose of about 40 mg per kg body mass, using a PEG 300 vehicle as a carrier. The plasma blood levels of compound 32 were measured over a 24 h period after oral administration. The results are shown in Table 5 below.

TABLE 5

| Time After Administration | | Plasma Concentration | |
|---|---|---|---|
| Hours | Minutes | (nM) | (ng/mL) |
| 0.28 | 17 | 1598 | 898 |
| 1.00 | 60 | 878 | 493 |
| 2.07 | 124 | 626 | 352 |
| 4.01 | 240 | 670 | 377 |
| 6.01 | 360 | 594 | 334 |
| 8.05 | 483 | 1115 | 627 |
| 12.04 | 722 | 246 | 138 |
| 14.08 | 845 | 102 | 57 |
| 24.00 | 1440 | 82 | 46 |

These results demonstrate that compound 32 maintains high blood levels (e.g., nearly 0.6 uM after 6 hours) long after oral administration. Although applicants do not wish to abound by any one particular theory, it is believed that the non-peptide structure of the compounds of the present invention make them less prone to biological (e.g., enzymatic) degradation, and thereby contribute to their prolonged blood levels after oral administration. From these data, the compounds of the present invention are predicted to have excellent oral bioavailability in humans, and maintain therapeutically significant blood levels over prolonged periods after oral administration.

EXAMPLE 17

This example demonstrates the influence of human protein binding on the antiviral activity of compound 32. Several potent and orally bioavailable HIV protease inhibitors failed to have in vivo antiviral efficacy. These failures have been ascribed, but not definitively proven, to be due to excessive binding to human plasma proteins, particularly serum albumin and AAG. The protein binding against human alpha acid glycoprotein (AAG, 10 μM) and against human serum albumin (HAS, 300 μM) were compared for compound 32 and amprenavir, a structurally related analog that is an FDA approved drug. The results are shown in Table 6.

TABLE 6

| | $IC_{50}$ (μM) | | |
|---|---|---|---|
| Compound | (−) | AAG | Alb |
| 32 | 0.0015 (1×) | 0.0022 (1.5×) | 0.003 (2×) |
| amprenavir | 0.029 (1×) | 0.18 (6×) | 0.021 (1×) |

These data demonstrate that the presence of AAG and HAS in physiologically excessive amounts does not adversely affect the antiviral activity of compound 32. From these data, the affinity of compound 32 for human AAG and HSA is predicted to be actually lower than that for amprenavir, a known drug. From these data, the compounds of the present invention are expected to have excellent in vivo efficacy in humans, and maintain therapeutically significant levels over prolonged periods of time.

EXAMPLE 18

Figure 5A:
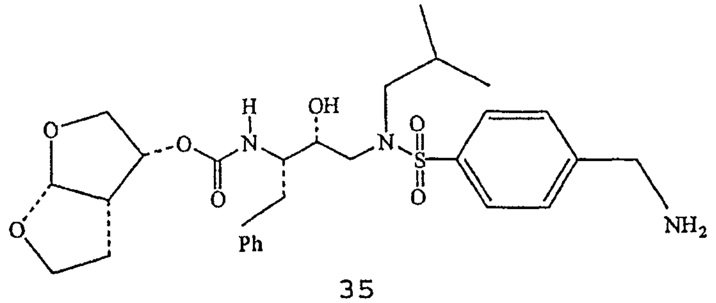
FIGS. 5A-5D illustrate the structures of particular compounds that were tested against various drug resistant HIV mutants.
Figure 5B:
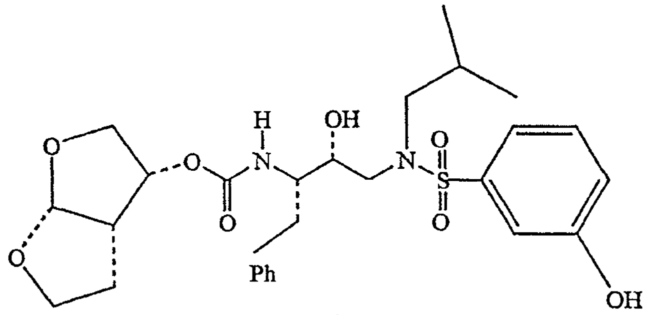
Figure 5C:
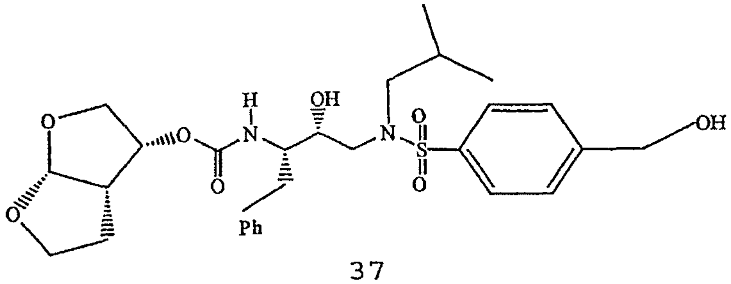
Figure 5D:
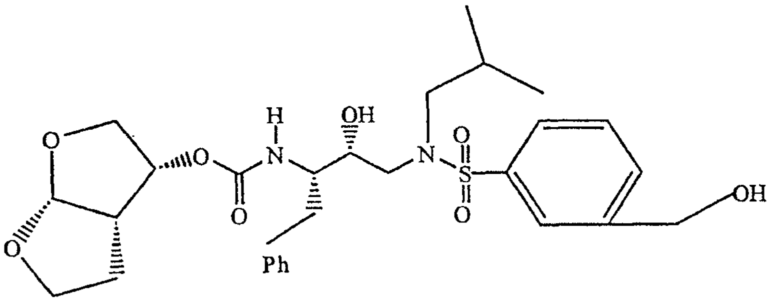

This example describes the inhibitory activity of compounds 35 (FIG. 5A), 36 (FIG. 5B), 37 (FIG. 5C) and 38 (FIG. 5D). In accordance with the technique disclosed in Example 13 above, the inhibitory activity of these compounds was tested against proteases of the wild-type HIV-1. Compound 36, 37 and 38 were also tested against proteases containing the deleterious drug resistance associated mutations V82F/I84V and G48V/V82A. Fitness was determined in accordance with Example 13. The results of these experiments are shown below in Table 7.

TABLE 7

| COMPOUND | ENZYME | $K_i$ (pM) | $K_{I\text{-}wt}/K_{I\text{-}mut}$ | Fitness |
|---|---|---|---|---|
| 35 | WT | 81 | 1 | |
| 36 | WT | 5< | | |
| | V82F/I84V | 24.4 | >4.9 | >0.8 |
| | G48V/V82A | 15.3 | >3.0 | >0.8 |
| 37 | WT | 12 | 1 | |
| | V82F/I84V | 25.7 | 2.1 | 0.3 |
| | G48V/V82A | 64 | 5.3 | 1.4 |
| 38 | WT | >5 | | |
| | V82F/I84V | 66.8 | >13 | >2.1 |
| | G84V/V82A | 34 | >6.8 | >1.8 |

These results further demonstrate compounds of the present invention that are potent inhibitors against mutant proteases. Based on the fitness profile, it is believed that drug resistant viruses containing the characteristic mutations assayed herein will not emerge from the wild-type in the presence of compound 37.

EXAMPLE 19

This example further demonstrates the broad-spectrum and potent activity of exemplary compounds of the present invention against multidrug-resistant clinical isolates.

The $IC_{50}$ values (μM) for all compounds 32, 35, 36, 37, and 38 were determined with respect to wild type clinical isolates HIV-$1_{LAI}$ and HIV-$1_{BaL}$. The latter is a monocytotropic strain of HIV.

The $IC_{50}$'s for isolates HIV-$1_{LAI}$ and HIV-$1_{Ba\text{-}L}$ were determined by exposing the PHA-simulated PBMC to HIV-1 (50 $TCID_{50}$ dose/1×$10^6$ PBMC), in the precence of various concentrations of compounds 32, 35, 36, 37 and 38, and using the inhibition of p24 Gag protein production as an endpoint on day 7 of culture ("p24 assay"). All drug sensitivities were performed in triplicate. The $IC_{50}$'s for isolate HIV-$1_{LAI}$ were also determined by exposing MT-2 cells (2×$10^3$) to 100 $TCID_{50}$s of HIV-$1_{LAI}$ cultured in the presence of various concentrations of compounds 32, 35, 36, 37 and 38. The $IC_{50}$'s were determined using the MTT assay on day 7 of culture. All sensitivities were determined in duplicate. The results are shown below in Table 8.

TABLE 8

| Virus | Cell Type/ Assay | Comp. 32 $IC_{50}$ (μM) | Comp. 35 $IC_{50}$ (μM) | Comp. 36 $IC_{50}$ (μM) | Comp. 37 $IC_{50}$ (μM) | Comp. 38 $IC_{50}$ (μM) |
|---|---|---|---|---|---|---|
| HIV-$1_{LAI}$ | MT-2/MTT | 0.00022 | 0.028 | 0.017 | 0.0053 | 0.028 |
| HIV-$1_{LAI}$ | PBMC/p24 | 0.00022 | 0.020 | 0.034 | 0.0027 | 0.0080 |
| HIV-$1_{Ba-L}$ | PBMC/p24 | 0.00033 | 0.013 | 0.038 | 0.0030 | 0.0093 |

These results demonstrate the potent antiretroviral activity of particular compounds of the present invention.

EXAMPLE 20

This example further illustrates the potent and broad-spectrum multidrug-resistant antiretroviral activity of an exemplary compound of the present invention.

Compound 32, shown in FIG. 3A, was tested against various mutant multidrug-resistant HIV-1 strains clinically isolated from patients. These isolates were all taken from patients who failed therapy on one or more HIV protease inhibitors due to high level clinical resistance. All of these isolates exhibit high level phenotypic resistance in antiviral assays against many of the commonly use HIV protease inhibitor drugs. Compound 32 was tested against these multidrug-resistant clinical isolates side-by-side with known drugs that are commonly used in HIV antiviral therapy, including reverse transcriptase inhibitors such as AZT, 3TC, DDI, DDC, and D4T, and protease inhibitors such as Indinavir (Ind.), Nelfinavir (Nel.), Ritonavir (Rit.), and Saquinavir (Saq.). The $IC_{50}$'s for compound 32 and the comparative drugs against the multidrug-resistant HIV-1 clinical isolates, and against wild-type HIV-1 (WT), are shown in Table 9a.

The mutant multidrug-resistant HIV-1 strains corresponding to each patient, numbered 9-35, were genetically analyzed in terms of the nucleic acid sequences of the protease (PR) and a portion of the reverse transcriptase (RT) genes from which mutations in these enzymes were determined. The mutations in the protease and reverse transcriptase of the multidrug-resistant viruses isolated from each patient are shown below in Table 9b.

TABLE 9a

| | $IC_{50}$ (μM) | | | | | | | | | |
|---|---|---|---|---|---|---|---|---|---|---|
| Patient Isolate | AZT | 3TC | DDI | DDC | D4T | Ind. | Nel. | Rit. | Saq. | Comp. 32 |
| 9 | 0.01 | 0.39 | 0.7 | 0.15 | 0.91 | 1.087 | 0.98 | 0.53 | >0.3125 | 0.0003 |
| 10 | 0.02 | 1.35 | 1.7 | 0.37 | 1.29 | >1.25 | >1.25 | 2.03 | >0.3125 | 0.0017 |
| 11 | 0.11 | 23.61 | 2.4 | 0.18 | 3.10 | 0.012 | 0.03 | 0.01 | 0.001 | 0.0004 |
| 12 | 0.07 | 0.78 | 0.9 | 0.20 | 1.23 | >1.25 | >1.25 | 2.47 | >0.3125 | 0.0010 |
| 13 | 0.17 | 1.04 | 0.5 | <0.1221 | 0.78 | >1.25 | 0.47 | 1.64 | >0.3125 | 0.0004 |
| 14 | 0.64 | | 2.4 | <0.1221 | 1.10 | 0.089 | 0.01 | 0.04 | 0.040 | 0.0003 |
| 15 | 0.20 | >31.25 | 2.2 | 0.32 | 1.10 | 0.265 | 0.47 | 1.14 | >0.3125 | 0.0011 |
| 16 | 0.97 | 27.98 | 3.5 | 0.57 | 1.81 | 0.384 | 0.86 | 1.34 | >0.3125 | 0.0031 |
| 17 | >1.25 | 28.05 | | 0.63 | 4.28 | 0.502 | 0.52 | 0.87 | 0.107 | 0.0022 |
| 18 | 0.55 | >31.25 | 2.2 | 0.48 | 2.08 | 0.369 | 0.60 | 3.02 | 0.039 | 0.0019 |
| 19 | >1.25 | >31.25 | 36.6 | 6.80 | 35.63 | 0.784 | 0.50 | 2.94 | 0.055 | 0.0005 |
| 20 | 1.25 | 3.21 | 7.1 | 0.57 | 22.54 | 0.591 | 0.58 | 1.90 | 0.032 | |
| 21 | >1.25 | 1.69 | 1 | 0.38 | 3.28 | 1.250 | >1.25 | 2.18 | 0.21 | 0.0023 |
| 22 | 1.02 | >31.25 | 3.7 | 0.63 | 4.68 | 0.173 | 0.10 | 0.56 | 0.003 | |
| 23 | 0.19 | >31.25 | 1.8 | 0.28 | 1.00 | 0.461 | 0.28 | 1.82 | 0.008 | 0.0004 |
| 24 | | | | | | | | | | 0.0004 |
| 25 | | | | | | | | | | 0.0019 |
| 26 | | | | | | | | | | 0.0019 |
| 27 | 0.03 | 1.72 | 2.6 | 0.41 | 4.00 | >1.25 | >1.25 | 2.97 | >0.3125 | 0.0009 |
| 28 | >1.25 | 2.08 | 2.8 | 0.36 | 5.44 | 1.040 | >1.25 | 2.66 | >0.3125 | |
| 29 | >1.25 | 2.24 | 3.8 | 0.34 | 5.29 | 0.569 | 0.67 | 0.36 | 0.050 | 0.0009 |
| 30 | 0.16 | >31.25 | 2.8 | 0.24 | 2.52 | 0.270 | 0.52 | 1.03 | 0.191 | 0.0019 |
| 31 | | >31.25 | 2.6 | <0.1221 | 3.11 | 0.251 | 0.24 | 0.85 | 0.074 | 0.0010 |
| 32 | 0.32 | >31.25 | 8.4 | 0.91 | 2.41 | 0.223 | 0.22 | 0.37 | >0.3125 | |
| 33 | 0.51 | >31.25 | 2.0 | 0.28 | 2.73 | 0.133 | 0.35 | 0.18 | 0.059 | 0.0005 |
| 34 | >1.25 | >31.25 | 9.1 | 1.13 | 7.71 | 0.595 | 0.26 | 3.38 | 0.063 | 0.0024 |
| 35 | 0.88 | >31.25 | 17.0 | 2.46 | 18.13 | 0.509 | 0.48 | 2.60 | 0.0616 | 0.0012 |
| (WT) | 0.022 | 0.264 | 0.895 | 0.243 | 1.059 | 0.02 | 0.031 | 0.019 | 0.007 | 0.0007 |

TABLE 9b

| Isolate | | Mutations | | | | | | | | | | | | |
|---|---|---|---|---|---|---|---|---|---|---|---|---|---|---|
| 9 | PR | V003I | L010I | S037N | R041K | G048V | I054S | I062V | L063S | 1064L | 1064L | A071V | V082A | 1093L |
| | RT | P004S | V0601 | V0901 | E122K | I135V | Q174K | Y181C | E194E/K | G196E | R211K | L214F | V245M | R227K |
| | | E297R | L301L/I | | | | | | | | | | | |
| 10 | PR | V003I | L010I | S037N | R041K | G048V | I054S | I062V | L063S | 1064L | 1064L | A071V | V082A | 1093L |
| | RT | P004S | V0601 | V0901 | E122K | I135V | T165A/T | Q174K | Y181C | E194K | G196E | R211K | L214F | H221H/Y |
| | | V245M | R277K | | | | | | | | | | | |
| 11 | PR | V003I | L010I | 1015V | M036I | S037N | R041K | L063T | I093L | | | | | |
| | RT | K020R/K | M041L | K043Q | E044D | V060I | D067N | T069D | E122E/K | D123E | Y181C/Y | M184V | G196E | H208Y |
| | | L210W | R211K | | | | | | | | | | | |
| 12 | PR | V003I | LQ10I | 1015V | K020R | M036I | S037N | R041K | G048V | I054T/I | L063T | A071V | T074A | V082A/V |
| | | 1093L | | | | | | | | | | | | |
| | RT | M041L | K043Q | E044D | V060I | D067N | T069D | L074L/I | K103N | D123E | I135T | Y181C | G196E | H208Y |
| | | L201W | R211K | | | | | | | | | | | |
| 13 | PR | V0031 | L010I | 1015V | K020R/K | M036I | S037N | R041K | G048V/G | I054T/I | Q058E/Q | Q061R/Q | L063T | A071A/V |
| | | 1072T/I | T074A/T | V082A | I093L | | | | | | | | | |
| | RT | M041L | K043Q | E044D | V060I | D067N | T069D | L074L/I | K103N | D123E | I135T/I | Y181C | G196E | H208Y |
| | | L210W | R211K | | | | | | | | | | | |
| 14 | PR | V003I | L010I | K020R | E035D | M036I | S037D | R041K | G048V | L063C | A071V | 1072T | V082A/V | 1093L |
| | RT | M041L | T069T/N | L074L/V | E122K | D123E | Y181C | Q207E | L210W | R211K | L214F | T215Y | L228R | E248D |
| | | R277K | E297K | | | | | | | | | | | |
| 15 | PR | V003I | L010I | E035D | R041K | L063P | A071A/V | I072V/I | G073R/C | V077I | 1084V | L090M | 1093L | |
| | RT | D067N | T069D | I142V | E169D | Y181C | M184V | Q207B | R211K | L214F | T215Y | D250E | P272A | Q278E |
| | | L283I | I293V | | | | | | | | | | | |
| 16 | PR | V003I | L010I | 1013V | E035D | S037A | R041K | L063P | A071V | G073S | I084V | L090M | | |
| | RT | K020R | M041L | K043N | D067N | D123N | D177E | I178M/I | M184V | G196E | E203D | L214F | T215Y | K219Q |
| | | R277K | G333E | | | | | | | | | | | |
| 17 | PR | V003I | L0101 | 1013V | E035D | S037A | R041K | L063P | A071V | G073G/S | I084V | L090M | | |
| | RT | K020R | M041L | K043N | D067N | D123N | D177E | I178M/I | M184V | G196E | E203D | L214F | T215Y | R277K |
| | | G333E | A360T | | | | | | | | | | | |
| 18 | PR | V003I | L010V | S037N | K043T | I054V | L063P | A071V | V082A | L090M | | | | |
| | RT | K020R | V035M | K064H | D067G | T069N | K070R | K102R/K | V1118I | E122K | I135T | S162A | M184V | T215S |
| | | D128E | K219Q | | | | | | | | | | | |
| 19 | PR | V003I | L010I | L0191 | S037Q | M046L | I054V | R057K | L063P | A071V | V082A | L090M | | |
| | RT | K020R | T058N | A062V | S068G | T069T/I | V075I | F077L | A098S | K103N | F116Y | I135T | I142M | Q151M |
| | | Y181C | M184V | | | | | | | | | | | |
| 20 | PR | V003I | L010I | T012P | K014R | I015V/I | G016E | S037N | M046I | I054V | K055R | I062V | L063N | A071T |
| | | V077I | V082A | I085V | L090M | | | | | | | | | |
| | RT | K020R | V0351 | T039A | M041L | K043E | E044A | D067N | V075A | K103N | V118I | I135M | Y181C | H208Y |
| | | L210W | R211K | | | | | | | | | | | |
| 21 | PR | V003I | L010I | 1015V | K020R | B035D | M036I | S037K | R041N | K043T/K | M041I | L063P | H609K | A071V |
| | | T074S | V082F | N088E | L084M | L090M | I093L | | | | | | | |
| | RT | K020R | V035T | T039R | M041L | K043E | E044D | V060I | I063M/I | D067N | T069D | A098G | V118I | D121H |
| | | I135T/I | I142V | | | | | | | | | | | |
| 22 | PR | V003I | L010I | E034E/Q | S037H | M046I | I054V | I062V | L063S | V082A | L089L/M | | | |
| | RT | K020R/K | T039A/T | M041L | K043E | E044D | D067N | V118I | M184V | E203E/K | Q207E | H208Y | L210W | R211K |
| | | L214F | T215Y | | | | | | | | | | | |
| 23 | PR | V003I | L010I | 1015V | K020I | L024I | M036I | S037N | I054V | R057K | L063P | A071V | V082A | |
| | RT | K011R | D067N | K070R | I135T | Y181V/D | M184V | D218E/D | K219Q | P272A | R277K | R284R/K | I293V | E297V |
| | | M357T/M | G359G/S | | | | | | | | | | | |

TABLE 9b-continued

| Isolate | | Mutations | | | | | | | | | | | | |
|---|---|---|---|---|---|---|---|---|---|---|---|---|---|---|
| 24 | PR | V003I | I015V | D030N | E035D | S037D | L063P | V077I | N088D | | | | | |
| | RT | K064R | E122K | D123S | D177E | M184V | G196R | R211G | L214F | V245T/M | E297A | I326V | I329L | T338S |
| | | N348I | R358K | | | | | | | | | | | |
| 25 | PR | V003I | K020I | T026T/I | S037N | M046I | L063P | A071V | G073S | V077I | I084V | L090M | I093L | |
| | RT | V035M | D067N | T069D | K070R | E122P | D177E | M184V | I202V | Q207E | R211K | L214F | T215F | K219Q |
| | | E224K | R277K | | | | | | | | | | | |
| 26 | PR | V003I | L010I | S037N | R041K | G048V | I054S | I062V | L063S | I064L | A071V | V082A | I093L | |
| | RT | P004S | V060I | V090I | E122K | I135Y | T135A/T | Q174K | Y181C | E194K | G196E | R211K | L214F | H221H/Y |
| | | V245M | R277K | | | | | | | | | | | |
| 27 | PR | V003I | L010I | I015V | K020R | M036I | S037N | R041K | G048V | I054T/I | L063T | A071A/V | T074A | V082A |
| | | I093L | | | | | | | | | | | | |
| | RT | M041L | K043Q | E044D | V060I | D067N | T069D | L074L/I | K103N | F116F/L | D123E | I135T | Y181C | G196E |
| | | H208Y | L210W | | | | | | | | | | | |
| 28 | PR | V003I | L010I | I015V | M036I | S037D | G048V | I054V | D060E | Q061E | I062V | I064V | A071V | V082A |
| | | L090M | I093L | | | | | | | | | | | |
| | RT | P004S | M041L | D067N | T069D | K070R | V090I | K103N | I135T | S162A | V179I | Y181C | G196E | Q207E |
| | | L214F | T215F | | | | | | | | | | | |
| 29 | PR | V003I | L010I | K020I | S037N | M046M/I | L063P | I072I/K | G073C | V077I | L090M | | | |
| | RT | V035I | T039A/E | M041L | E044D | L074L/V | R083K | K102Q | S162C | I178L | E203K | H208Y | L210W | R211K |
| | | L214F | T215Y | | | | | | | | | | | |
| 30 | PR | V003I | L010I | E035D | R041K | L063P | A071A/V | I072V/I | G073G/S | V0771 | I084V/I | L090M | I093L | |
| | RT | D067N | T069D | I142V | E169D | Y181C | M184V | Q207E | R211K | L214F | T215Y | D250E | P272A | Q278E |
| | | L283I | I293V | | | | | | | | | | | |
| 31 | PR | V003I | L010L/I | E035D | M036M/I | S037N | M046X | I054V | L063P | I066F | A071V | V082A/T | I084V/I | |
| | RT | K032R/K | K064R | D067N | K070R | K103N/K | E122K | Y181F/C | M184V | R211K | L214F | D218E | K219Q | E248D |
| | | T286A | I293V | | | | | | | | | | | |
| 32 | PR | V003I | L010I | S037N | G048V | I054V | I062V/I | L063P | A071A/T | V077I | V082A | I093L | | |
| | RT | K020R | M041L | D123N | I178L | M184V | T200A/T | E203D | Q207E | L210L/W | L214F | T215Y | R277K | T286A |
| | | Q334L/Q | T338S/T | | | | | | | | | | | |
| 33 | PR | V003I | L010I | E035D | M036I | S037D | D060E | L063P | I064V | I084V | L090M | | | |
| | RT | M041L/M | D067N | T063T/N | K070R | D177D/E | M184V | I202V | Q207E | L210W | R211K | L214F | T215Y | K219Q |
| | | V245T | P272A | | | | | | | | | | | |
| 34 | PR | V003I | L010V | S037N | K043T | I054V | L063P | A071V | V082A | L090M | | | | |
| | RT | K020R | V035M | K064H | D067G | T069N | K070R | K102R/K | V1181I | E122K | I13ST | S162A | M184V | T215S |
| | | D218E | K219Q | | | | | | | | | | | |
| 35 | PR | V003I | L010I | L019I | S037Q | M046L | I054V | R057K | L063P | A071V | V082A | L090M | | |
| | RT | K020R | T058N | A062V | S068G | T069T/I | V075I | F077L | A098S | K103N | F116Y | I135T | I142M | Q151M |
| | | Y181C | M184V | | | | | | | | | | | |

The results of this experiment further show the effectiveness of an exemplary compound of the present invention against a wide range of viral mutants compared to other well-known inhibitors. These mutant viruses represent a panel of the most broadly cross resistant clinical isolates known to date based on their resistance to therapeutically used HIV protease inhibitors. Compound 32 was consistently potent against all of the clinically isolated mutant viruses tested, and was significantly more potent against these multidrug resistant viruses than the comparative drugs which are currently used in human HIV-1 therapy. Compound 32 was ten to one-thousand times more potent against these viruses than even saquinavir, one of the most potent known compounds against multidrug-resistant HIV-1. Based on the high potency, it is believed that these mutants will not only be inhibited, but also that these mutants would not be able to emerge if the compound is administered to a patient infected with a predecessor virus.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of preventing the development of protease inhibitor resistance in an HIV-infected mammal, the method comprising administering to the HIV-infected mammal a protease inhibitor resistance-inhibiting effective amount of a compound selected from:

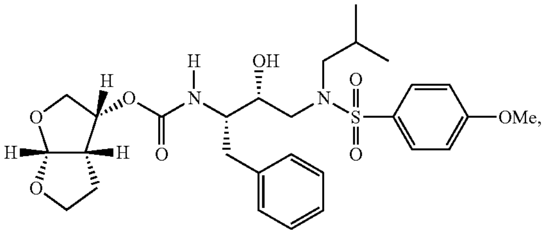 [SMILES: COc1ccc(S(=O)(=O)N(CC(C)C)C[C@@H](O)[C@H](Cc2ccccc2)NC(=O)O[C@H]2CO[C@H]3OCC[C@H]32)cc1]

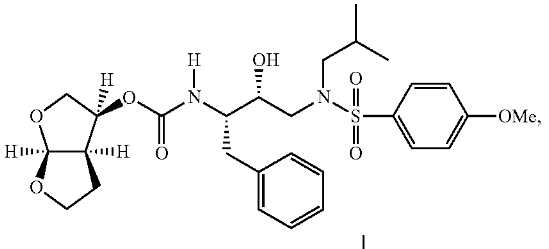

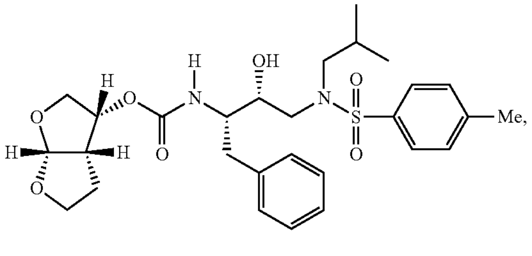

-continued

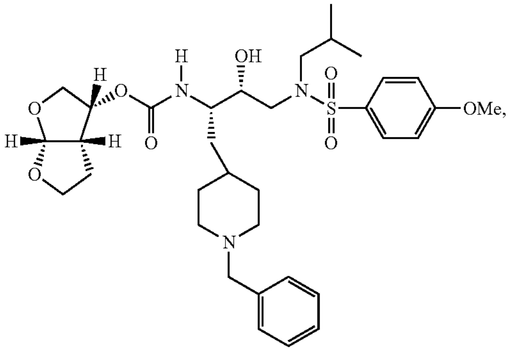

and

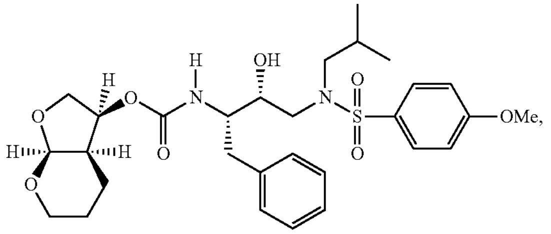

wherein the protease inhibitor resistance-inhibiting effective amount is an amount sufficient to produce an in vivo protease inhibitor concentration or level in which a mutant virus that is capable of evolving from the HIV virus infecting the mammal has lower fitness, relative to the HIV virus infecting the mammal, in the presence of the compound.

2. The method of claim 1, which comprises further administration of at least one other antiviral agent selected from the group consisting of ritonavir, indinavir, amprenavir and saquinavir.

3. The method of claim 2, wherein the one other antiviral agent is ritonavir.

4. A method of preventing the development of protease inhibitor resistance in an HIV-infected mammal, the method comprising administering to the HIV-infected mammal a protease inhibitor resistance-inhibiting effective amount of a compound of the formula:

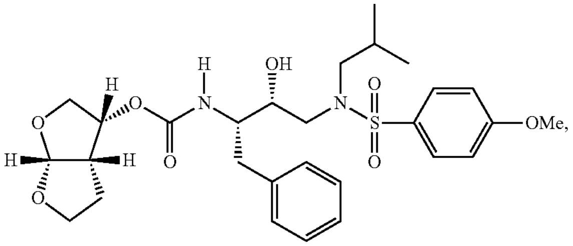 [SMILES: COc1ccc(S(=O)(=O)N(CC(C)C)C[C@@H](O)[C@H](Cc2ccccc2)NC(=O)O[C@H]2CO[C@H]3OCC[C@H]32)cc1]

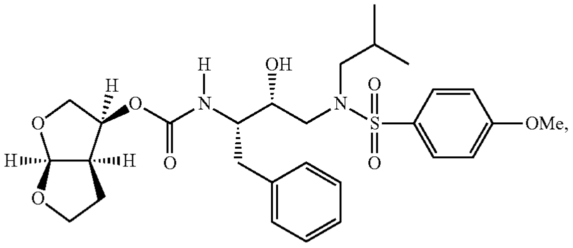

-continued

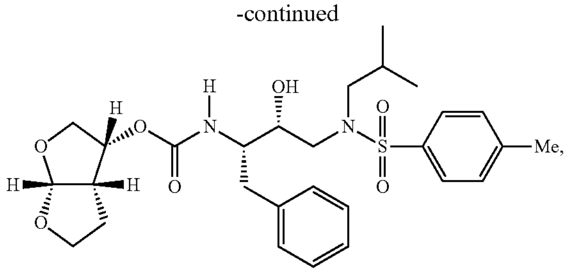

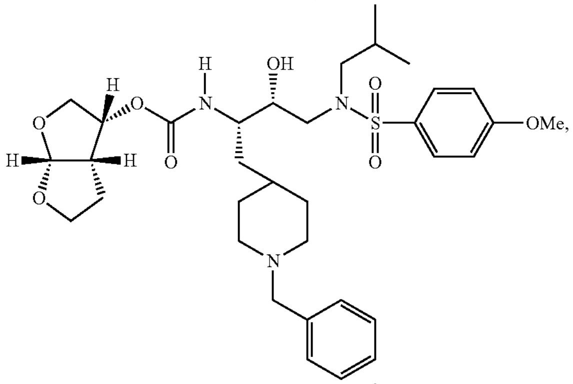

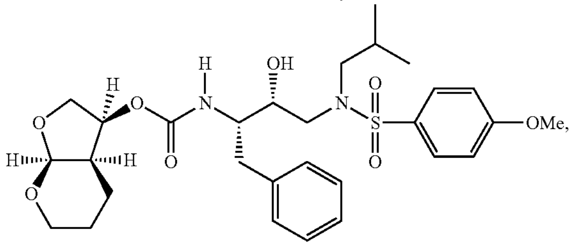

and

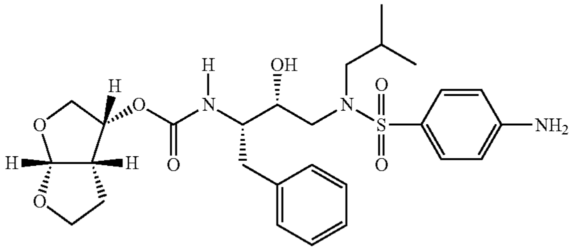

wherein the protease inhibitor resistance-inhibiting effective amount is an amount sufficient to produce an in vivo protease inhibitor concentration or level in which a mutant virus that is capable of evolving from the HIV virus infecting the mammal has lower fitness, relative to the HIV virus infecting the mammal, in the presence of the compound, and wherein the method comprises further administration of at least one antiviral agent selected from the group consisting of ritonavir, indinavir, amprenavir and saquinavir.

5. The method of claim 1, wherein the compound is:

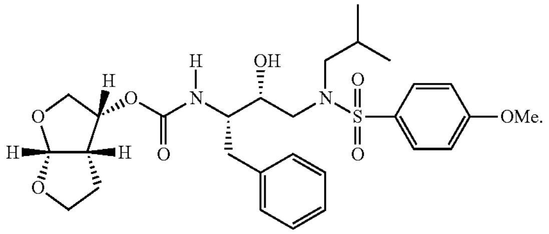

6. The method of claim 4, wherein the compound is:

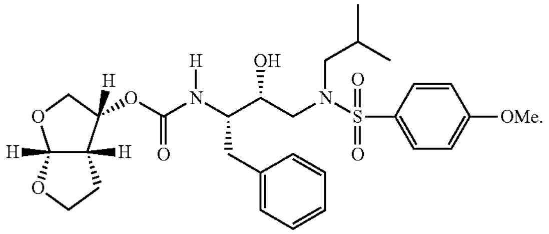

* * * * *